(12) United States Patent
Gelfand et al.

(10) Patent No.: US 9,534,221 B2
(45) Date of Patent: Jan. 3, 2017

(54) TARGETING THE STEROIDOGENIC PATHWAY FOR TREATING AND/OR PREVENTING ALLERGIC DISEASES

(71) Applicant: National Jewish Health, Denver, CO (US)

(72) Inventors: Erwin W. Gelfand, Cherry Hills Village, CO (US); Meiqin Wang, Glendale, CO (US); Yi Jia, Centennial, CO (US)

(73) Assignee: National Jewish Health, Denver, CO (US)

( * ) Notice: Subject to any disclaimer, the term of this patent is extended or adjusted under 35 U.S.C. 154(b) by 0 days.

(21) Appl. No.: 14/160,747

(22) Filed: Jan. 22, 2014

(65) Prior Publication Data

US 2014/0206749 A1    Jul. 24, 2014

Related U.S. Application Data

(60) Provisional application No. 61/755,311, filed on Jan. 22, 2013.

(51) Int. Cl.

| | |
|---|---|
| *A61K 31/451* | (2006.01) |
| *C12N 15/113* | (2010.01) |
| *A61K 31/444* | (2006.01) |
| *A61K 31/58* | (2006.01) |
| *A61K 31/7105* | (2006.01) |

(52) U.S. Cl.
CPC ......... *C12N 15/1137* (2013.01); *A61K 31/444* (2013.01); *A61K 31/451* (2013.01); *A61K 31/58* (2013.01); *A61K 31/7105* (2013.01); *C12N 2310/14* (2013.01); *C12Y 114/15006* (2013.01); *Y10S 514/826* (2013.01)

(58) Field of Classification Search
None
See application file for complete search history.

(56) References Cited

U.S. PATENT DOCUMENTS

2008/0279812 A1    11/2008 Boyd et al.

FOREIGN PATENT DOCUMENTS

WO    WO 2007/103162    9/2007

OTHER PUBLICATIONS

"Allergies", Mayo Clinic, Aug. 2014, downloaded on Feb. 8, 2016 from www.mayoclinic.org/diseases-conditions/allergies/basics/definition/CON-20034030, pp. 1-8 of 8.*
Calderon et al. "T-cell cytokine profiles are altered in childhood asthma exacerbation." Respirology, Jan. 2009, vol. 14, No. 2, pp. 264-269.
Jia et al. "Steroidogenic enzyme Cyp11a1 regulates Type 2 CD8+ T cell skewing in allergic lung disease." PNAS, May 2013, vol. 110, No. 20, pp. 8152-8157.
Miyahara et al. "Contribution of antigen-primed CD8+ T cells to the development of airway hyperresponsiveness and inflammation is associated with IL-13." The Jounal of Immunology, Feb. 2004, vol. 172, No. 4, pp. 2549-2458.
Pazirandeh et al. "Paracrine glucocorticoid activity produced by mouse thymic epithelial cells." FASEB, May 1999, vol. 13, No. 8, pp. 893-901.
Wang et al. "The steroidogenic enzyme Cyp11a1 is essential for development of peanut-induced intestinal anaphylaxis." J Allergy Clin Immunol., Jul. 2013, vol. 13, No. 5, pp. 1174-1183.
International Search Report and Written Opinion for International (PCT) Patent Application No. PCT/US2014/012479, mailed Apr. 14, 2014 12 pages.
International Preliminary Report on Patentability for International (PCT) Patent Application No. PCT/US2014/012479, mailed Aug. 6, 2015 9 pages.
Database Medline [online] US National Library of Medicine, Bethesda, MD, US; Feb. 1996, Turner et al. "The role of endogenous corticosterone in the late-phase response to allergen challenge in the brown Norway rat.", Database accession No. NLM8564095, 1 page.
Database Medline [online] US National Library of Medicine, Bethesda, MD, US; Dec. 1987, Sasaki et al. "Late asthmatic response to Ascaris antigen challenge in dogs treated with meyrapone.", Database accession No. NLM3688649, 1 page.
Noti et al. "TNF suppresses acute intestinal inflammation by inducing local glucocorticoid synthesis," The Journal of Experimental Medicine, May 2010, vol. 207, No. 5, pp. 1057-1066.
Yu et al. "Effects of Evodiamine and Rutaecarpine on the Secretion of Corticosterone by Zona Fasciculata-Reticularis Cells in Male Rats," Journal of Cellular Biochemistry, Oct. 2009, vol. 108, No. 2, pp. 469-475.
Zhang et al. "Effects of endogenous glucocorticoids on allergic inflammation and TH1/TH2 balance in airway allergic disease," Annals of Allergy, Asthma & Immunology, Dec. 2009, vol. 103, No. 6, pp. 525-534.
Corrected Search Report for European Patent Application No. 14742818.9, dated Sep. 28, 2016, 10 pages.

* cited by examiner

*Primary Examiner* — Savitha Rao
*Assistant Examiner* — Gregg Polansky
(74) *Attorney, Agent, or Firm* — Sheridan Ross P.C.

(57) ABSTRACT

The present invention relates to methods and compositions for treating and/or preventing allergic diseases or conditions by inhibiting one or more components of the steroidogenic pathway.

14 Claims, 23 Drawing Sheets

Figure 5
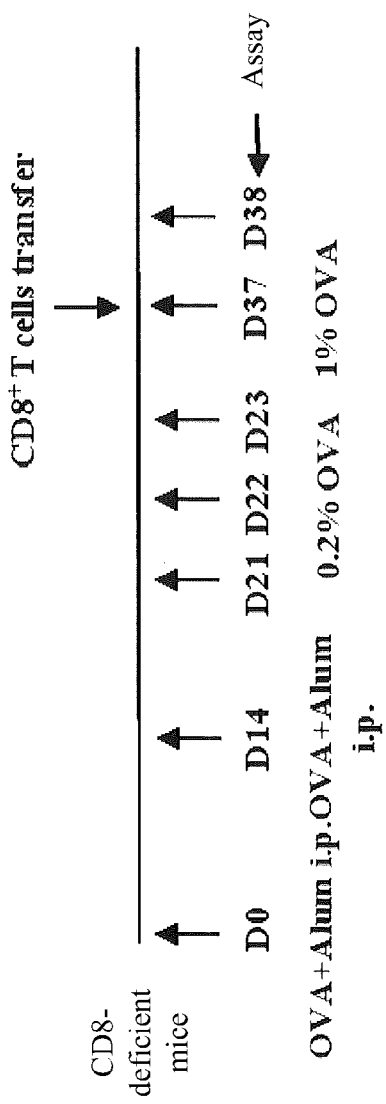
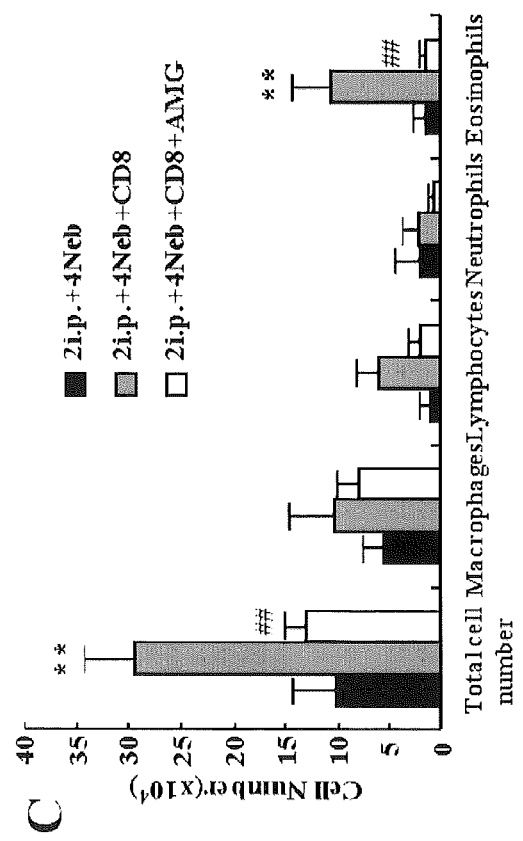
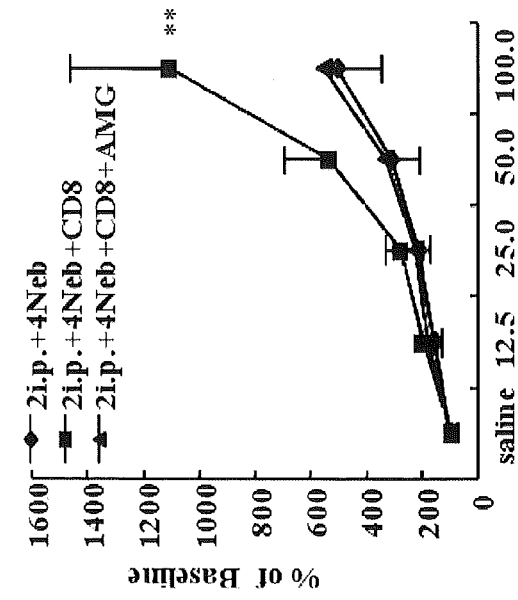

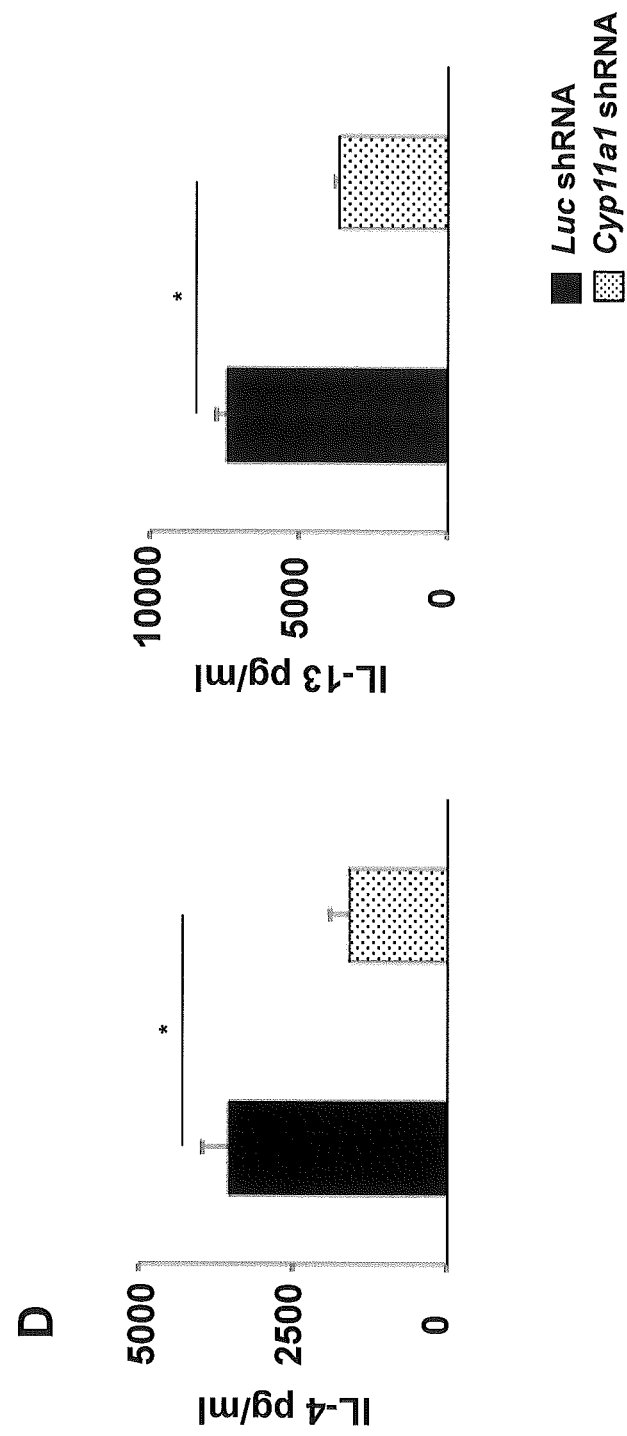
Figure 11 continue

TARGETING THE STEROIDOGENIC PATHWAY FOR TREATING AND/OR PREVENTING ALLERGIC DISEASES

CROSS REFERENCE TO RELATED APPLICATION

This application claims the benefit of priority under 35 U.S.C. §119(e) to U.S. Provisional Patent Application Ser. No. 61/755,311, filed Jan. 22, 2013, which is incorporated herein by reference.

GOVERNMENT SUPPORT

This invention was made with Government support under grant numbers P01 HL 036577, and R01 AI-77609, awarded by the National Institutes of Health. The Government of the United States has certain rights in the invention.

REFERENCE TO A SEQUENCE LISTING

This application contains a Sequence Listing submitted electronically as a text file by EFS-Web. The text file, named "Seq_Listing_2879-126_ST25", has a size in bytes of 1 KB, and was recorded on Jan. 22, 2014. The information contained in the text file is incorporated herein by reference in its entirety pursuant to 37 CFR §1.52(e)(5).

FIELD OF INVENTION

The present invention generally relates to methods and compositions for treating and/or preventing allergic diseases or conditions by inhibiting one or more components of the steroidogenic pathway including but not limited to proteins, enzymes, receptors, and protein by-products of the steroidogenic pathway.

BACKGROUND OF THE INVENTION

Steroid hormones, including glucocorticoids (GCs), play an important role in the regulation of the immune system (Chrousos, G. P., N. Engl. J. Med. 332, 1351-1362 (1995)). Endogenous glucocorticoid synthesis is controlled by the hypothalamic-pituitary-adrenal axis (Chrousos, G. P., N. Engl. J. Med. 332, 1351-1362 (1995); Rhen, T., & Cidlowski, J. A., N. Engl. J. Med. 353, 1711-1723 (2005)) and is regulated by the transcriptional control of steroidogenic enzymes of the cytochrome P450 gene family (Mueller, M., et al. J. Exp. Med. 203, 2057-2062 (2006)). Corticosteroids have been used in treating allergic diseases due to their anti-inflammatory activity (Barnes, P J. Br. J. Pharmacol. 163:29-43 (2011)), but, somewhat paradoxically, increasing evidence indicates that corticosteroids may also enhance disease pathogenesis by activating and enhancing growth of CD4 T cells and inhibiting Th1 cytokine production (Cima, I., Fuhrer, A., & Brunner, T. Immunol. Lett. 106, 99-102 (2006)). Glucocorticoids amplified immune responses in steroid-insensitive $CD8^+$ T cells (Ohnishi, H., et al. J. Allergy Clin. Immunol. 121, 864-871 (2008)). As well, the corticosteroids themselves may induce Th2 cytokine production while simultaneously suppressing the production of Th1 cytokines (Koya, T. et al. J. Immunol. 179, 2787-2796 (2007)).

The inhibitory role of GCs on immune cells is well characterized (De Bosscher, K., et al. Endocr. Rev. 24, 488-522 (2003); De Bosscher, K, & Haegeman, G. Mol. Endocrinol. 23, 281-291 (2009)). GCs reduce inflammation through inhibition of NF-κB and by inducing the expression of anti-inflammatory proteins including annexin 1 and MAPK phosphatase 1 (Chrousos, G. P. N. Engl. J. Med. 332, 1351-1362 (1995)). GCs and other synthetic derivatives have been used to treat a variety of diseases, including inflammatory diseases of the intestine and asthma (Barnes, P J. Br. J. Pharmacol. 163:29-43 (2011); Faubion, W. A. Jr., et al. Gastroenterology 121, 255-260 (2001)). Although the anti-inflammatory activity of GCs is well described, accumulating evidence suggests that GCs can also enhance immune cell activation, inducing gene transcription and promoting the pathogenesis of allergic diseases (Cima, I., et al. J. Exp. Med. 200, 1635-1646 (2004); Ohnishi, H., et al. J. Allergy Clin. Immunol. 121, 864-871 (2008)). Steroid hormones are mainly produced in the adrenal glands, but other tissues also produce GCs through the induction of steroidogenic enzymes (Chrousos, G. P. N. Engl. J. Med. 332, 1351-1362 (1995); Payne, A. H. Biol. Reprod. 42, 399-404 (1990)). The intestinal mucosa contains steroidogenic enzymes such as cytochrome P450, family 11, subfamily A, polypeptide 1 (Cyp11a1) and synthesizes potent GCs which exhibit both an inhibitory and a co-stimulatory role on intestinal T cell activation (Cima, I., et al. J. Exp. Med. 200, 1635-1646 (2004)).

Cyp11a1 (also known as P450scc) is a key regulator of steroid biogenesis as the first and rate-limiting enzyme in the steroidogenic pathway, converting cholesterol to pregnenolone (Pazirandeh, A., et al. FASEB J. 13, 893-901 (1999)). Induction of the Cyp11a1 promoter by epidermal growth factor involves a ras/MEK1/AP-1-dependent pathway (Croft, M. et al. J. Exp. Med. 180, 1715-1728 (1994)). Cyp11a1 is expressed primarily in the cortex of the adrenal gland, but testis, ovary, placenta, thymus, and intestine also express Cyp11a1 (Cima, I., et al. J. Exp. Med. 200, 1635-1646 (2004); Pazirandeh, A., et al. FASEB J. 13, 893-901 (1999)). Activation of Cyp11a1 results in a spectrum of steroid hormones, including glucocorticoids that are known to play a role in T cell function (Mosmann, T. R., and Coffman, R. L. Annu. Rev. Immunol. 7, 145-173 (1989); Seder, R. A. et al. J. Immunol. 148, 1652-1656 (1992)). Several of the gonadal steroids have been shown to have important immune effects on T cells that express their cognate receptors. T cells express receptors for androgen and estrogen and receptor activation can impact cytokine gene transcription. These studies have related gender bias to differences in the response of CD4, CD8, and T regulatory cells (De Bosscher, K., et al. Endocr. Rev. 24, 488-522 (2003); De Bosscher, K, & Haegeman, Mol. Endocrinol. 23, 281-291 (2009)). T cells also express many of the steroid metabolic enzymes (De Bosscher, K., et al. Endocr. Rev. 24, 488-522 (2003)). Depletion of Cyp11a1 in mice or rabbits results in steroid deficiency, female external genitalia, and death (Shih, M. C., et al. Mol. Cell. Endocrinol. 336, 80-84 (2011); Pang, S., et al. Endocrinology 131, 181-186 (1992); Yang, X., et al. Endocrinology 132, 1977-1982 (1993)). In humans, mutations in the Cyp11a1 gene result in a steroid hormone deficiency, causing a rare and potentially fatal form of lipoid congenital adrenal hyperplasia (Kim, C. J., et al. J. Clin. Endocrinol. Metab. 93, 696-702 (2008); Al Kandari, H., et al. J. Clin. Endocrinol. Metab. 91, 2821-2826 (2006)). Patients with a heterozygous or homozygous mutation of Cyp11a1 exhibit adrenal insufficiency and sex reversal (Tajima, T., et al. J. Clin. Endocrinol. Metab. 86, 3820-3825 (2001); Parajes, S., et al. J. Clin. Endocrinol. Metab. 96, E1798-E1806 (2011)).

Transcription factors such as Steroidogenic Factor-1 (SF-1), Activator Protein 2 (AP-2), and several tissue-specific GATA family proteins enhance the transcription of Cyp11a1 through interactions with AP-1, specificity Protein-1 (SP-1) and AP-2 (National Asthma Education and Prevention Program (National Heart Lung and Blood Institute) Third Expert Panel on the Management of Asthma. National Center for Biotechnology Information (U.S.). Expert panel report 3 guidelines for the diagnosis and management of asthma. Bethesda, Md.: National Institutes of Health National Heart Lung and Blood Institute; 2007). In particular, the GATA protein family plays an important role in the regulation of Cyp11a1 expression (Barnes, P J. *Br J. Pharmacol.* 163:29-43 (2011)). GATA binding elements have been identified in the Cyp11a1 promoter and Cyp11a1 expression was decreased in GATA3-deficient mice (Wei, G, et al. *Immunity* 35, 299-311 (2011)). GATA4 significantly upregulated Cyp11a1 expression in granulosa cells (Sher, N., et al. *Mol. Endocrinol.* 21, 948-962 (2007)). These results identify important events in the transcriptional regulation of Cyp11a1 that directly affect steroid synthesis and release.

CD4 Th cells play a pivotal role in the induction and control of allergic inflammation, including food allergy (Islam, S. A., & Luster, A. D. *Nature Med.* 18, 705-715 (2012)). In a mouse model of food allergy, allergen-specific CD4 T cells were activated in the mesenteric lymph nodes and recruited to the small intestine, resulting in increased levels of Th2 cytokines in the inflamed small intestine (Knight, A. K., et al. *Am. J. Physiol. Gastrointest. Liver Physiol.* 293, G1234-G1243 (2007)).

In humans, allergen-specific Th2 CD4 T cells are essential in the development and maintenance of both type I IgE-mediated and non-IgE-mediated food allergic responses. In patients with anaphylactic peanut allergy, increased numbers of peanut-specific IL-5- and IL-4-producing Th2 cells are found in peripheral blood (Prussin, C., et al. *J. Allergy Clin. Immunol.* 124, 1326-1332 (2009)). In addition, peanut-specific T cell lines from individuals with peanut anaphylaxis primarily produce Th2 cytokines (IL-4, IL-13) (DeLong, J. H., et al. *J. Allergy Clin. Immunol.* 127, 1211-1218 (2011)). Other food allergies were also characterized by increased levels of Th2 cytokines; in patients with milk-induced gastrointestinal diseases, milk-specific CD4 T cells derived from the duodenal mucosa produce high levels of Th2 cytokines, especially IL-13 (Beyer, K., et al. *J. Allergy Clin. Immunol.* 109, 707-713 (2002)).

Allergic asthma is a heterogeneous inflammatory disorder of the airways characterized by chronic airway inflammation and airway hyperresponsiveness (AHR) (Kim, H. Y., et al. *Nat. Immunol.* 11, 577-584 (2011); Holgate, S. T. *Nat. Med.* 18, 673-683 (2012)). Numbers of $CD8^+IL-13^+$ T cells are increased in asthmatics (Gelfand, E. W. and Dakhama, A. *J. Allergy Clin. Immunol.* 117, 577-582 (2006)) and during the development of experimental asthma in mice (Hamelmann, E. et al. *J. Exp. Med.* 183, 1719-1729 (1996); Miyahara, N. et al. *J. Immunol.* 172, 2549-2558 (2004); Miyahara, N. et al. *J. Immunol.* 174, 4979-4984 (2005)). In an atopic environment rich in IL-4, these $CD8^+$ T cells mediate asthmatic responses (Koya, T. et al. *J. Immunol.* 179, 2787-2796 (2007)). However, the mechanisms regulating the conversion of $CD8^+$ effector T cells from IFN-γ to pathogenic IL-13-producing effector cells have not been defined.

Asthma has increased dramatically over the past 50 years and now affects 5-10% of the population in many developed countries (Kim, H. Y., et al. *Nat. Immunol.* 11, 577-584 (2011)). National and international guidelines recommend the use of inhaled corticosteroids as the first step in controlling airway inflammation and symptoms in persistent asthma (Holgate, S. T. *Nat. Med.* 18, 673-683 (2012); Gelfand, E. W. and Dakhama, A. *J. Allergy Clin. Immunol.* 117, 577-582 (2006)). However, it has been demonstrated that 45% of steroid-naive asthmatic patients do not respond to inhaled corticosteroids. Corticosteroid insensitivity has been adopted as a principal criterion for characterizing asthma severity (Hamelmann, E. et al. *J. Exp. Med.* 183, 1719-1729 (1996)). Increased numbers of $CD8^+$ T cells, which are more resistant than $CD4^+$ T cells to corticosteroids (Miyahara, N. et al. *J. Immunol.* 172, 2549-2558 (2004); Miyahara, N. et al. *J. Immunol.* 174, 4979-4984 (2005)), have been detected in steroid-insensitive asthmatics (Koya, T. et al. *J. Immunol.* 179, 2787-2796 (2007)) and have correlated with lower lung function (LaVoie, H. A. and King, S. R. Exp. Biol. Med. 234, 880-907 (2009)). The inventors and others also found that numbers of $CD8^+IL-13^+$ cells were increased in experimental asthma models in mice (Shih, M. C. et al. *Mol. Endocrinol.* 22, 915-923 (2008); National Asthma Education and Prevention Program (National Heart Lung and Blood Institute) Third Expert Panel on the Management of Asthma. National Center for Biotechnology Information (U.S.). Expert panel report 3 guidelines for the diagnosis and management of asthma. Bethesda, Md.: National Institutes of Health National Heart Lung and Blood Institute; 2007, Guidelines for the diagnosis and management of asthma. Bethesda, Md.: National Institutes of Health National Heart Lung and Blood Institute; 2007) as a result of their activation by IL-4-producing $CD4^+$ T cells (Martin, R. J. et al. *J. Allergy Clin. Immunol.* 119, 73-80 (2007)). $CD8^+$ T cells can be polarized to effector subsets with cytokine profiles similar to those found in $CD4^+$ T cells (Li, L. B. et al. *Blood* 110, 1570-1577 (2007); Payne, A. H. *Biol. Reprod.* 42, 399-404 (1990); van Rensen, E. L. et al. *Am. J. Respir. Crit. Care Med.* 172, 837-841 (2005)). Both in vivo and in vitro, IL-4 is capable of triggering $CD8^+$ T cell differentiation from a predominant IFN-γ-producing cell to one producing IL-13. However, the mechanisms underlying this conversion of $CD8^+$ T cells is unknown.

Transcriptional profiling identified Cyp11a1 transcripts as one of the most highly up-regulated during the differentiation of $CD8^+$ T lymphocytes to a Tc2 phenotype, that is, a CD8 T cell capable of IL-13 production. This upregulation of Cyp11a1 in $CD8^+$ T cells is similar to the upregulation seen in $CD4^+$ T cells in a peanut allergy model, suggesting that this enzyme is essential in $CD4^+$ and $CD8^+$ T cells for pro-allergic differentiation.

$CD4^+$ T cell differentiation into Th2 cells with production of IL-4, IL-5, IL-9, and IL-13 has been shown to be critical for the development of altered airway responsiveness and eosinophilic airway inflammation in experimental models of asthma (Samy, T. S. et al. *Endocrinology* 142, 3519-3529 (2001); Pottratz, S. T. et al. *J. Clin. Invest.* 93, 944-950 (1994)). In addition to $CD4^+$ T cells, $CD8^+$ T cells can be polarized to effector subsets with cytokine profiles similar to those found in $CD4^+$ T cells (Payne, A. H. *Biol. Reprod.* 42, 399-404 (1990); van Rensen, E. L. et al. *Am. J. Respir. Crit. Care Med.* 172, 837-841 (2005)). It has been previously demonstrated that there is an important role for type 2 (Tc2) $CD8^+$ T cells in the development of experimental asthma (Slominski, A. et al. *FEBS J.* 273, 2891-2901 (2006)) as a result of their activation by IL-4-producing $CD4^+$ T cells (Martin, R. J. et al. *J. Allergy Clin. Immunol.* 119, 73-80 (2007)). Increased expression of BLT1 (leukotriene B4 receptor) on the surface of $CD8^+$ T cells leads to their increased accumulation in the lungs (Guidelines for the diagnosis and management of asthma. Bethesda, Md.: National Institutes of Health National Heart Lung and Blood Institute; 2007). Both human (Miyahara, N. et al. *J. Immunol.* 172, 2549-2558 (2004)) and mouse (Miyahara, N. et al. *J. Immunol.* 174, 4979-4984 (2005)) CD8$^+$ T cells demonstrate an insensitivity to corticosteroids not seen in CD4$^+$ T cells, supporting the notion that CD8$^+$ T cells are at the root of the failure of asthmatics to respond to corticosteroids and may be responsible for persistent AHR and inflammation (Koya, T. et al. *J. Immunol.* 179, 2787-2796 (2007)). In asthmatics, numbers of CD8$^+$ T cells in the airways have correlated with lower airway function (LaVoie, H. A. and King, S. R. Exp. Biol. Med. 234, 880-907 (2009)).

Current therapies for allergic asthma have been fairly restricted with few new drugs introduced into the clinic in the last decade. Inhaled corticosteroids have remained the main anti-inflammatory agent for asthma. Indeed, upwards of 40-50% of asthmatics fail to respond to inhaled corticosteroids with changes in FEV1 (Hamelmann, E. et al. *J. Exp. Med.* 183, 1719-1729 (1996)). Moreover, corticosteroids may also enhance disease pathogenesis, especially amplifying responses in the steroid-insensitive population of CD8$^+$ T cells (Miyahara, N. et al. *Nature Med.* 10, 865-869 (2004)). Corticosteroids may induce Th2 cytokine production while suppressing the production of Th1 cytokines. A combination of steroid insensitivity and plasticity of CD8$^+$ T cells may be major contributors to the failure of some patients to respond to corticosteroids. CD8$^+$BLT1$^+$IL-13$^+$ CD8$^+$ T cells have been proposed to be a primary cause of the airway inflammation and hyperresponsiveness seen in asthma (National Asthma Education and Prevention Program (National Heart Lung and Blood Institute) Third Expert Panel on the Management of Asthma. National Center for Biotechnology Information (U.S.). Expert panel report 3 guidelines for the diagnosis and management of asthma. Bethesda, Md.: National Institutes of Health National Heart Lung and Blood Institute; 2007, Guidelines for the diagnosis and management of asthma. Bethesda, Md.: National Institutes of Health National Heart Lung and Blood Institute; 2007). However, the mechanism underlying the conversion of CD8$^+$ T cells from IFN-γ-producing cells to IL-13 producing cells remains unclear.

SUMMARY OF THE INVENTION

One embodiment of the invention relates to a method of treating or preventing an allergic disease in a subject who has, or is at risk of developing an allergic disease, comprising administering a therapeutically effective amount of a steroidogenic pathway inhibitor.

In one aspect, the allergic disease can be selected from an allergic lung disease, allergen-induced airway hyperresponsiveness, allergen-induced inflammation, rhinitis, asthma, allergic rhinitis, food allergy, eosinophilic esophagitis, chronic urticaria, atopic dermatitis, occupational allergy, allergic conjunctivitis, hay fever, airborne allergic sensitivities, stinging insect allergy, hypersensitivity pneumonitis, eosinophilic lung diseases, inflammatory bowel disease, ulcerative colitis, and Crohn's disease.

In one aspect, the allergic disease is caused by one or more proteinaceous allergens.

In another aspect, the subject has been sensitized to an allergen or is at risk of becoming exposed to an allergen.

In one aspect, the food allergy is peanut allergy.

In yet another aspect, the allergic disease is an allergic lung disease.

The steroidogenic pathway inhibitor can be selected from an antibody, an antisense molecule, an siRNA molecule, an shRNA molecule, a receptor antagonist, a chemical entity, a nucleotide, a peptide, and a protein. In one aspect, the steroidogenic pathway inhibitor inhibits one or more enzymes, receptors or protein by-products of the steroidogenic pathway. In another aspect, the steroidogenic pathway inhibitor inhibits cytochrome P450 family 11 subfamily A polypeptide 1 (Cyp11A1). In still another aspect, the steroidogenic pathway inhibitor is aminoglutethimide or a Cyp11A1 siRNA or shRNA molecule. In yet another aspect, the steroidogenic pathway inhibitor inhibits 3βHSD. In still yet another aspect, the steroidogenic pathway inhibitor is trilostane. In another aspect, the steroidogenic pathway inhibitor inhibits cytochrome P450 family 11 subfamily β polypeptide 1 (Cyp11β1). In yet another aspect, the steroidogenic pathway inhibitor is metyrapone.

Another embodiment of the invention relates to a method of inhibiting T-cell pro-allergic differentiation in a subject comprising administering a therapeutically effective amount of a steroidogenic pathway inhibitor. In one aspect, the T-cell pro-allergic differentiation is CD4+ T-cells to Th2 and Th17 cell differentiation. In yet another aspect, the T-cell pro-allergic differentiation is CD8+ T-cells to Tc2 cell differentiation. In still another aspect, the T-cell pro-allergic differentiation is IL4-induced conversion of CD8+ T-cells into IL-13 secreting cells. In another aspect, the T-cell pro-allergic differentiation is IL-4 induced conversion of CD4+ T-cells into IL-13 secreting cells.

Various embodiments of the invention are described below. However, the invention is not limited to embodiments described in this summary, as inventions described in the description that follows are also expressly encompassed.

DETAILED DESCRIPTION OF THE INVENTION

This invention generally relates to methods for the prevention and/or treatment of an allergic disease or condition, as well as methods of inhibiting T-cell pro-allergic differentiation in subjects who have or are risk of developing an allergic disease or condition. The invention includes administration of a therapeutically effective amount of a steroidogenic pathway inhibitor. The invention includes the use of a composition comprising a steroidogenic pathway inhibitor as well as the composition itself. The invention also includes kits that contain one or more steroidogenic pathway inhibitors.

Figure 15:
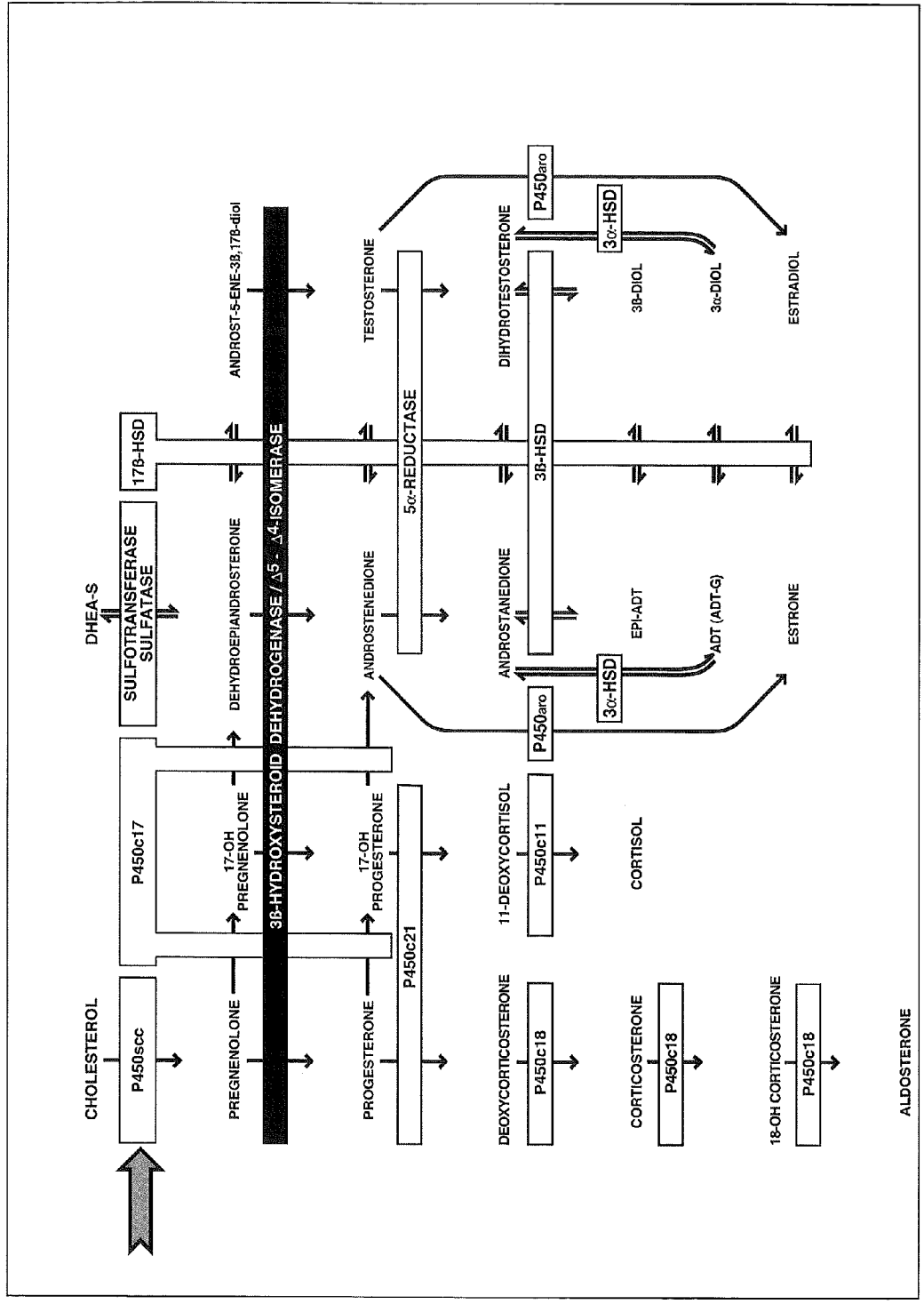
FIG. 15 shows a schematic representation of the major mammalian steroidogenic pathway(s) (from Simard et al., Endocrine Rev, June 2005, 26(4):525-82).
Figure 16:
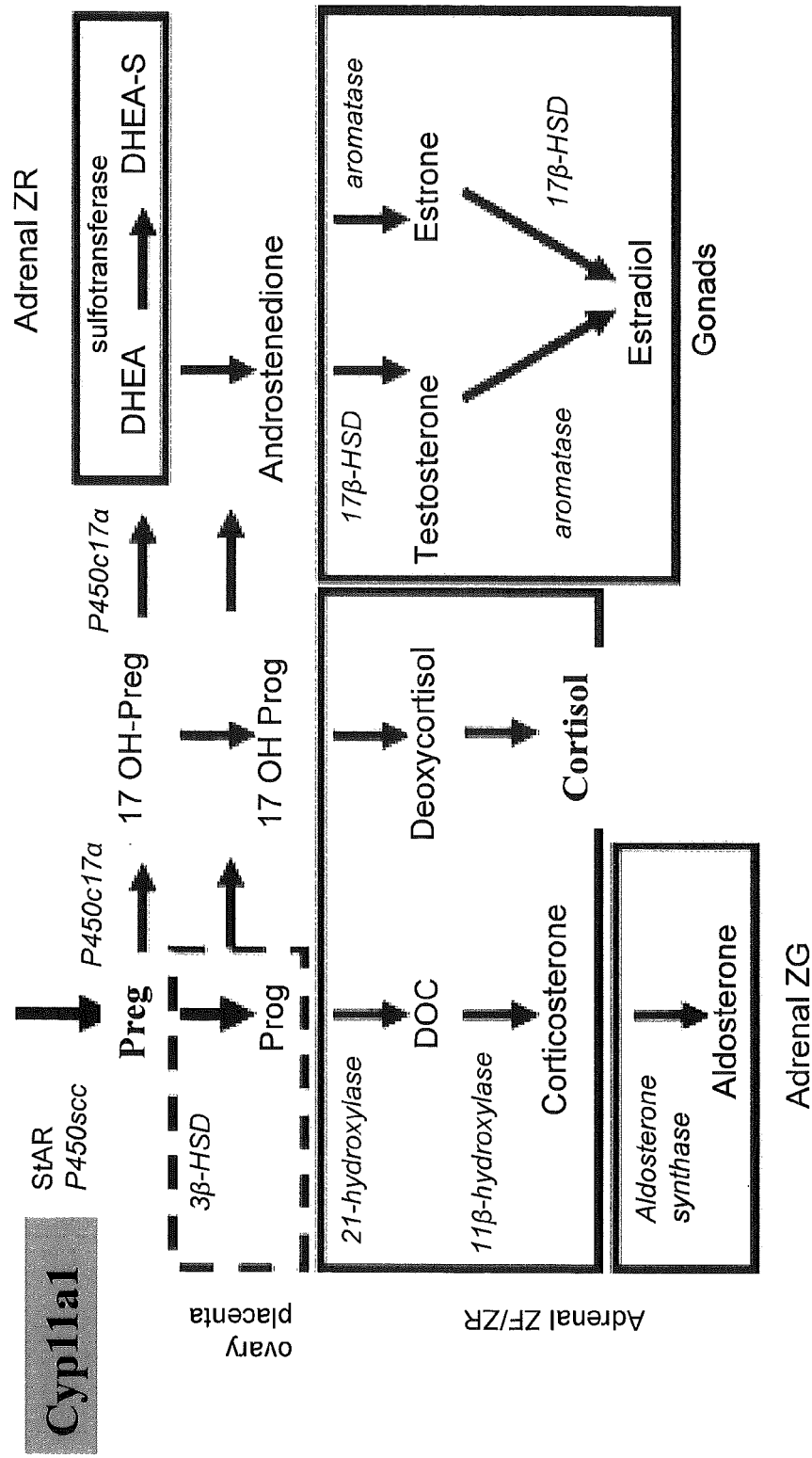
FIG. 16 shows an overview of steroidogenesis.
Figure 17:
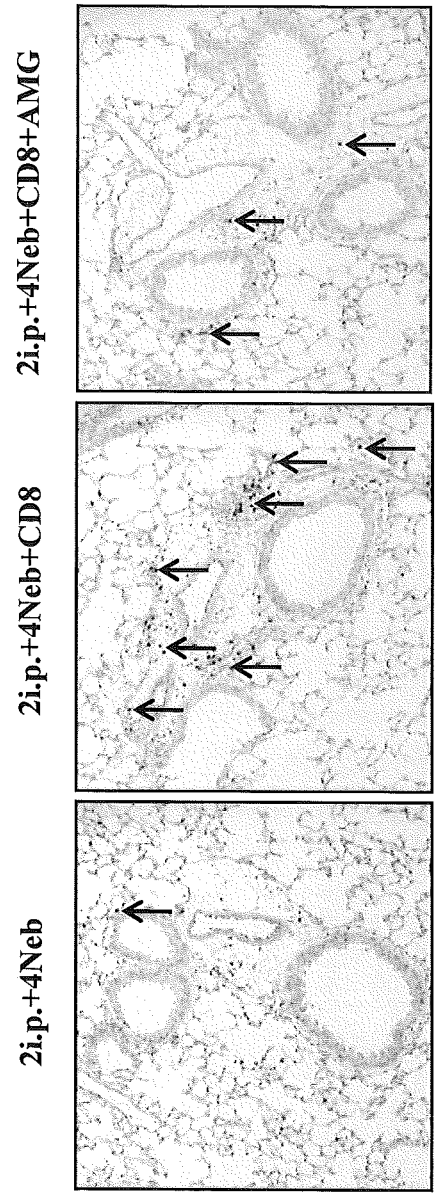
FIG. 17 shows representative photomicrographs of immunohistochemical staining for Cyp11a1-positive cells in the lung (×200). The lungs were from secondary challenged CD8-deficient recipients, secondary challenged CD8-deficient recipients of 5×10⁶ IL-2-differentiated CD8⁺ T cells, and secondary challenged CD8-deficient recipients of 5×10⁶ IL-2-AMG-differentiated CD8⁺ T cells.

Steroid hormones play a critical role in the differentiation, development, growth, and physiological function of most vertebrate tissues. The major pathways of steroid hormone synthesis are well established, and the sequence of the responsible steroidogenic enzymes has been elucidated (Simard et al., Endocrine Rev. June 2005, 26(4):525-82; see also FIGS. 15 and 16). Many of the enzymes of the steroidogenic pathway are localized to the smooth endoplasmic reticulum (ER) with the exceptions of P450scc (i.e. P450 cholesterol side-chain cleavage; CYP11A1), P450c11 (CYP11B1), and aldosterone synthase (CYP11B2) (Simard et al., *Endocrine Rev.* June 2005, 26(4):525-82).

Many inhibitors of the various components of the steroidogenic pathway are known including but not limited to aminoglutethimide (inhibits Cyp11A1), trilostane (inhibits β3HSD—also known as 3-β-HSD; or 3-β-hydroxysteroid dehydrogenase/Δ-5-4 isomerase) and metyrapone (inhibits Cyp11β1).

In the present invention, the inventors demonstrate the role of Cyp11a1 in controlling IL-4-mediated CD8⁺ T cell conversion in vitro and in vivo. The inventors demonstrate that mRNA transcript levels, protein levels, and the enzyme activity of Cyp11a1 in CD8⁺ T cells are all increased surprisingly following differentiation in the presence of IL-2+IL-4 compared to IL-2 alone. Further, the Cyp11a1 enzyme inhibitor aminoglutethimide (AMG) or knock-down of Cyp11a1 protein levels using a specific shRNA (small or short hairpin RNA), blocked the functional conversion of CD8⁺ T cells from IFN-γ- to IL-13-producing cells. Expression of the lineage-specific transcription factors T-bet or GATA3 was not affected by inhibition of Cyp11a1 activity, indicating that it was downstream of expression of these master regulatory transcription factors. Adoptive transfer of AMG-treated CD8⁺ T cells, in contrast to untreated CD8⁺ T cells, failed to restore AHR and inflammation in sensitized and challenged CD8-deficient mice. The inventors demonstrate for the first time Cyp11a1 as a key regulator of CD8⁺ pro-allergic Tc2 cell differentiation and plasticity.

CD8⁺ T cells have been primarily associated with production of IFN-γ; however, in the presence of IL-4, CD8⁺ T cells were skewed to differentiate into IL-13-producing cells. This differentiation was associated with increases in GATA3 and decreases in T-bet expression and was dependent on antigen signaling through the T cell receptor. Although IL-4 triggered the up-regulation of Cyp11a1 mRNA, protein, and enzymatic activity, the function of Cyp11a1 enzymatic activation was downstream of GATA3 and T-bet transcriptional events as their expression levels were unaffected by blocking Cyp11a1 activity with AMG Since addition of SIINFEKL (SEQ ID NO:1) was also required for IL-13 cytokine production (FIG. 2C), it thus appeared that T-cell receptor signaling and activation of Cyp11a1 enzymatic activity were both required for the later stages in CD8 skewing to a Tc2 (IL-13) phenotype.

Taken together, the data presented herein establish for the first time that the steroidogenic enzyme Cyp11a1 plays a direct role in the polarization of CD8⁺ T cells from an IFN-γ- to an IL-13-producing effector cell and, as a result, is a critical regulator of the development of lung allergic responses. Cyp11a1 thus represents a pivotal enzyme linking steroidogenesis in T cells to pro-allergic differentiation pathways.

The inventors also demonstrate that peanut sensitization and challenge not only results in inflammatory and cytokine changes in the small intestine but that mRNA, protein, and enzymatic activity levels of the steroidogenic enzyme Cyp11a1 are also markedly elevated. Administration of an inhibitor of Cyp11a1 enzymatic activity, AMG, prevented development of allergic diarrhea and accumulation of inflammatory cells in the small intestine in a dose-dependent manner. Levels of serum pregnenolone were reduced in parallel. AMG treatment decreased IL13 and IL17 mRNA expression in the small intestine without impacting Cyp11a1 mRNA or protein levels. In vitro, the inhibitor decreased levels of IL13 and IL17 mRNA in polarized Th2 and Th17 CD4 T cells, respectively, without affecting levels of GATA3, RORγt, or the polarization of Th1 cells, IFNG, and T-bet expression. The importance of Cyp11a1 was further demonstrated using shRNA-mediated silencing of Cyp11a1 in polarized Th2 CD4 T cells which resulted in significantly decreased levels of IL-4 and IL-13 mRNA and protein. These data demonstrate that Cyp11a1 played an important role in the development of peanut allergy through its effects on steroidogenesis, a critical pathway in CD4⁺ T cell Th2 differentiation.

The inventors demonstrate for the first time that levels of Cyp11a1 protein and mRNA are increased in the jejunum of sensitized and challenged mice. In parallel, enzymatic activity is increased as demonstrated by increased levels of pregnenolone in the serum of sensitized and challenged mice. The inventors also demonstrate that Cyp11a1 enzymatic activity is essential for induction of peanut allergy using an inhibitor, AMG Administration of this inhibitor during the oral challenge phase, after sensitization, results in significantly lower serum pregnenolone levels and reduces the incidence and severity of diarrhea and intestinal inflammation (mast cell accumulation and goblet cell metaplasia), accompanied by decreases in IL13 and IL17A mRNA in the intestine. The inhibitor did not alter the development of specific antibodies, including peanut-specific IgE, likely because sensitization was completed prior to treatment in the challenge phase. Although administration of the inhibitor in vivo could not identify specific target cells, these data demonstrated for the first time that Cyp11a1 functions as a key regulator of the development of peanut-induced allergic responses.

The data described in the Examples presented herein demonstrate that inhibition of Cyp11a1 significantly reduces CD4⁺ Th2 and Th17 cytokine production in vivo. Interestingly, the inhibitor does not affect expression of the Th1, Th2, and Th17 lineage-specific transcription factors T-bet (Th1-specific T box transcription factor), GATA3 (GATA-binding factor 3), or RORγt (RAR-related orphan receptor gamma t). The results support that suppression of Th2 and Th17 cytokine production is not mediated through effects on lineage-specific transcription factor expression but on cytokine transcription. The primary action of Cyp11a1 enzymatic activity manifests downstream of these lineage-specific transcription factors.

Further, the function of Cyp11a1 in CD4 T cells, Th1, Th2, and Th17 polarization was monitored in vitro in the presence of AMG. The highest levels of Cyp11a1 protein and enzymatic activity were detected in polarized Th2 cells, with significantly lower levels in Th17 cells, and virtually no activity in Th1 cells. The inhibitor decreased IL-13 cytokine production in polarized Th2 cells; however, IFN-γ production was not affected by the inhibitor in polarized Th1 cells. Similar to the in vivo data, the inhibitor did not affect GATA3 mRNA expression in polarized Th2 cells nor levels of T-bet or RORγt in polarized Th1 and Th17 cells, respectively. Thus, inhibition of Cyp11a1 enzymatic activity impaired CD4 Th2 and Th17 cell differentiation, which in turn decreased production of the Th2 cytokine (IL-13) and Th17 cytokine (IL-17A) and these effects were mediated downstream of their respective and essential lineage-specific transcription factors.

Additionally, Cyp11a1 mRNA was silenced in cultured Th2 CD4 T cells using a short hairpin RNA (shRNA) to demonstrate that the results with AMG were specific to inhibition of Cyp11a1. During Th2 polarization, cells were transduced with retrovirus expressing Cyp11a1-targeted shRNA or control (luc) shRNA and activated under Th2 conditions. Cyp11a1 shRNA decreased the expression of Cyp11a1 mRNA levels by 58%±5.2% and enzymatic activity of Cyp11a1, monitoring pregnenolone levels, was reduced by 47%±4.5%. Levels of Th2 cytokine (IL4, IL13) mRNA and protein were decreased upon transduction of Cyp11a1 shRNA. As we observed with Cyp11a1 inhibition in vivo and in vitro with AMG, levels of GATA3 mRNA remained unaffected after silencing of Cyp11a1. These data confirmed in vivo and in vitro AMG inhibition data, demonstrating that Cyp11a1 critically regulates Th2 cell differentiation and cytokine production.

These studies demonstrate for the first time that activation of the steroidogenic enzyme Cyp11a1 plays a critical role in the development of intestinal allergic responses through its effects on CD4$^+$ Th2 polarization and IL-13 production. Cyp11a1 thus is a novel target for the regulation and treatment of peanut-induced allergy.

According to the present invention, allergic diseases and/or conditions, include but are not limited to pulmonary conditions such as allergic lung disease, allergic rhinitis, asthma, airway hyperresponsiveness, allergen-induced airway hyperresponsiveness and hay fever as well as other allergic conditions including but not limited to a food allergy, allergen-induced inflammation, eosinophilic esophagitis, chronic urticaria, atopic dermatitis, occupational allergy, allergic conjunctivitis, airborne allergic sensitivities, stinging insect allergy, hypersensitivity pneumonitis, eosinophilic lung diseases, inflammatory bowel disease, ulcerative colitis, Crohn's disease and drug allergies. Symptoms of the allergies, including but not limited to diarrhea and intestinal inflammation as well as asthma and airway hyperresponsiveness, is apparently or obviously, directly or indirectly triggered by an allergen to which a subject has previously been sensitized. In one aspect, the allergic disease or condition can be caused by one or more proteinaceous allergens. Sensitization to an allergen refers to being previously exposed one or more times to an allergen such that an immune response is developed against the allergen. Responses associated with an allergic reaction, including but not limited to histamine release, edema, vasodilatation, bronchial constriction, airway inflammation, airway hyperresponsiveness, asthma, allergic rhinitis (hay fever), nasal congestion, sneezing, running nose, skin rash, diarrhea including acute allergic diarrhea and intestinal inflammation), typically do not occur when a naive subject is exposed to the allergen for the first time, but once a cellular and humoral immune response is produced against the allergen, the subject is "sensitized" to the allergen. Allergic reactions then occur when the sensitized individual is re-exposed to the same allergen (e.g., an allergen challenge). Once a subject is sensitized to an allergen, the allergic reactions can become worse with each subsequent exposure to the allergen, because each re-exposure not only produces allergic symptoms, but further increases the level of antibody produced against the allergen and the level of T cell response against the allergen.

According to the present invention, inflammation is characterized by the release of inflammatory mediators (e.g., cytokines or chemokines) which recruit cells involved in inflammation to a tissue. A condition or disease associated with allergic inflammation is a condition or disease in which the elicitation of one type of immune response (e.g., a Th2-type immune response) against a sensitizing agent, such as an allergen, can result in the release of inflammatory mediators that recruit cells involved in inflammation in a subject, the presence of which can lead to tissue damage and sometimes death. A Th2-type immune response is characterized in part by the release of cytokines which include IL-4, IL-5, and IL-13. A TH17-type response is characterized by the release of IL-17. The present invention is particularly useful for treating allergen-induced food allergies (such as peanut allegories) and airway hyperresponsiveness and airway inflammation, including, allergen-induced asthma and rhinitis.

Accordingly, various embodiments of the present invention include treating a subject that has been sensitized to an allergen and has been or is at risk of becoming exposed to the allergen. In other embodiments, the present invention includes preventing an allergic disease or condition in a subject at risk of becoming exposed to the allergen. Such allergens can be related to a food, a plant, a gas, a pathogen, a metal, a glue or a drug. Examples of food allergens include but are not limited to groundnuts such as peanuts; nuts from trees including Brazilian nuts, hazelnuts, almonds, walnuts; fruit, milk, eggs, fish, shellfish, wheat, or gluten. Examples of plant allergens include but are not limited to pollen, trees, grass, weeds, ragweed, poison Oak or poison ivy. Examples of gas allergens include but are not limited to environmental tobacco smoke, and carbon monoxide. Examples of pathogen allergens include but are not limited to mold, viruses or bacteria. Examples of metal allergens include but are not limited to lead, nickel, chromate, or cobalt. Examples of drug allergens include but are not limited to penicillin, sulfur, or aspirin. Additional allergens include but are not limited to latex, dust mites, pet dander (skin flakes), droppings from cockroaches, rodents and other pests or insects.

According to the present invention, "airway hyperresponsiveness" or "AHR" refers to an abnormality of the airways that allows them to narrow too easily and/or too much in response to a stimulus capable of inducing airflow limitation. AHR can be a functional alteration of the respiratory system resulting from inflammation in the airways or airway remodeling (e.g., such as by collagen deposition). Airflow limitation refers to narrowing of airways that can be irreversible or reversible. Airflow limitation or airway hyperresponsiveness can be caused by collagen deposition, bronchospasm, airway smooth muscle hypertrophy, airway smooth muscle contraction, mucous secretion, cellular deposits, epithelial destruction, alteration to epithelial permeability, alterations to smooth muscle function or sensitivity, abnormalities of the lung parenchyma and infiltrative diseases in and around the airways. Many of these causative factors can be associated with inflammation. AHR can be triggered in a patient with a condition associated with the above causative factors by exposure to a provoking agent or stimulus. Such stimuli include, but are not limited to, an allergen.

According to the present invention, treatment of a subject having an allergic disease and/or condition can commence as soon as it is recognized (i.e., immediately) by the subject or by a clinician that the subject has been exposed or is about to be exposed to an allergen. Additionally, preventing an allergic disease or condition can commence prior to the subject being exposed to an allergen. Treating the subject and/or preventing an allergic disease or condition in the subject, can comprise administering a composition including but not limited to a small molecule inhibitor, an antibody, a chemical entity, a nucleotide, a peptide, a protein, an antisense molecule, and siRNA molecule, and shRNA molecule that inhibits one or more proteins, and/or protein-by-products, enzymes, and/or receptors of the steroidogenic pathway. Inhibiting a component of the sterodogenic pathway includes both direct inhibition of the components as well as inhibition of the expression of the one or more components of the pathway. Inhibition of one or more components of the steroidogenic pathway can be by any mechanism, including, without limitations, decreasing activity of one or more components, increasing inhibition of one or more of the components, degradation of one or more of components, a reduction or elimination of expression of one or more components and combinations thereof. Binding to one or more component to prevent its wild-type enzymatic activity for example, including competitive and noncompetitive inhibition, inhibiting transcription, and regulating expression can also inhibit the component. These inhibitors can also reduce expression of $CD4^+$ and $CD8^+$ T cell proliferation and have the ability to suppress Th2 differentiation and/or Th17 differentiation.

The present invention also relates to a method of inhibiting T-cell pro-allergic differentiation in a subject by administering to the subject a therapeutically effective amount of a steroidogenic pathway inhibitor. In one aspect, the T-cell pro-allergic differentiation is CD4+ T-cells to Th2 and Th17 cell differentiation. In another aspect, the T-cell pro-allergic differentiation is CD8+ T-cells to Tc2 cell differentiation. The T-cell pro-allergic differentiation can be IL-4 induced conversion of CD8+ T-cells into IL-13 secreting cells. In still another aspect, the T-cell pro-allergic differentiation can be IL-4 induced conversion of CD4+ T-cells into IL-13 secreting cells.

In accordance with the present invention, acceptable protocols to administer a composition including the route of administration and the effective amount of a composition to be administered to a subject can be determined by those skilled in the art. The composition of the present invention can be administered in vivo or ex vivo. Suitable in vivo routes of administration can include, but are not limited to, aerosol, oral, nasal, inhaled, topical, intratracheal, transdermal, rectal, or parenteral routes. Preferred parenteral routes can include, but are not limited to, subcutaneous, intradermal, intravenous, intramuscular, or intraperitoneal routes.

In one embodiment, the method of treating and/or preventing an allergic disease and/or condition or inhibiting T-cell pro-allergic differentiation can comprise administering a therapeutically effective amount of a composition comprising a compound that interacts with a regulator of a component of the steroidogenic pathway including but not limited to Cyp11a1 mRNA expression or Cyp11a1 protein expression. In one aspect, the regulator is an inhibitor of the steroidogenic pathway, including but not limited to an antibody, an antisense molecule, an siRNA molecule, an shRNA molecule, a receptor antagonist, a chemical entity, a nucleotide, a peptide and a protein. In one aspect, the steroidogenic pathway inhibitor inhibits one or more enzymes, receptors, or protein by-products of the steroidogenic pathway. In a preferred embodiment, the steroidogenic pathway inhibitor inhibits Cyp11A. This inhibitor can be aminoglutethimide, a Cyp11A siRNA molecule or a Cyp11A shRNA molecule. In other aspect, the steroidogenic pathway inhibitor inhibits 3βHSD and can be triostane. In still another aspect, the steroidogenic pathway inhibitor inhibits Cyp11β1 (cytochrome P450 family 11 subfamily β polypeptide 1) and can be metyrapone.

According to the methods of the present invention, a therapeutically effective amount of a steroidogenic pathway inhibitor or a composition comprising a steroidogenic pathway inhibitor that is administered to a subject, comprises an amount that is capable of inhibiting expression and/or activity of one or more components of the steroidogenic pathway (mRNA and/or protein) without being toxic to the subject. An amount that is toxic to a subject comprises any amount that causes damage to the structure or function of a subject (i.e., poisonous).

The invention also includes kits that contain one or more steroidogenic pathway inhibitors.

In addition, according to the present invention, the composition as well as the kits of the present invention, can comprise a pharmaceutically acceptable excipient. According to the present invention, the composition, may be administered with a pharmaceutically acceptable carrier, which includes pharmaceutically acceptable excipients and/or delivery vehicles, for delivering the agent to a subject (e.g., a liposome delivery vehicle). As used herein, a pharmaceutically acceptable carrier refers to any substance suitable for delivering a therapeutic composition useful in the method of the present invention to a suitable in vivo or ex vivo site. Preferred pharmaceutically acceptable carriers are capable of maintaining the composition of the present invention in a form that, upon arrival of the composition to a target cell, the composition is capable of entering the cell and inhibiting one or more components of the steroidogenic pathway (mRNA and/or protein) in the cell. Suitable excipients of the present invention include excipients or formularies that transport or help transport, but do not specifically target a nucleic acid molecule to a cell (also referred to herein as non-targeting carriers). Examples of pharmaceutically acceptable excipients include, but are not limited to water, phosphate buffered saline, Ringer's solution, dextrose solution, serum-containing solutions, Hank's solution, other aqueous physiologically balanced solutions, oils, esters, glycols and combinations thereof. Aqueous carriers can contain suitable auxiliary substances required to approximate the physiological conditions of the recipient, for example, by enhancing chemical stability and isotonicity.

Suitable auxiliary substances include, for example, sodium acetate, sodium chloride, sodium lactate, potassium chloride, calcium chloride, and other substances used to produce phosphate buffer, Tris buffer, and bicarbonate buffer. Auxiliary substances can also include preservatives, such as thimerosal, m- or o-cresol, formalin and benzol alcohol. Compositions of the present invention can be sterilized by conventional methods and/or lyophilized.

According to the methods of the present invention, the subject can be any animal subject, and particularly, in any vertebrate mammal, including, but not limited to, primates, rodents, livestock or domestic pets. Preferred mammals for the methods of the present invention include humans.

The following examples are provided for illustrative purposes, and are not intended to limit the scope of the invention as claimed herein. Any variations which occur to the skilled artisan are intended to fall within the scope of the present invention. All references cited in the present application are incorporated by reference herein to the extent that there is no inconsistency with the present disclosure.

EXAMPLES

Examples 1-6 demonstrate the role of Cyp11a1 in controlling IL-4-mediated CD8+ T cell conversion in vitro and in vivo.

Materials and Methods for Examples 1-6

Animals

OT-1 TCR transgenic (OT-1) mice and homozygous CD8-deficient mice were bred in the animal facility at National Jewish Health (Denver, Colo.). OT-1 mice (C57BL/6 strain) express a transgenic TCR specific for SIINFEKL peptide (ovalbumin (OVA)$_{257-264}$). CD8-deficient mice were generated by targeting the CD8+-chain gene in C57BL/6 mice (Oka, H. et al. *Cell. Immunol.* 206, 7-15 (2000); Sundrud, M. S, and Nolan, M. A. *Curr. Opin. Immunol.* 22, 286-292 (2010)). Animal experiments in this study were conducted under a protocol approved by the Institutional Animal Care and Use Committee of National Jewish Health.

CD8+ T Cell Culture

CD8+ effector memory T cells were generated in vitro as previously described (Miyahara, N. et al. *J. Immunol.* 172, 2549-2558 (2004); Miyahara, N. et al. *J. Immunol.* 174, 4979-4984 (2005)). In brief, mononuclear cells (MNCs) were processed from the spleens of OT-1 mice followed by stimulation of 1 μg/ml SIINFEKL peptide (SEQ ID NO:1) was used to stimulate cells for 1.5 hours. Two days after culture, living cells were re-isolated using histopaque and cultured in complete RPMI 1640 medium that contained recombinant mouse IL-2 (20 ng/ml) (R&D, Minneapolis, Minn.) or IL-2+IL-4 (20 ng/ml) (Peprotech, Rocky Hill, N.J.). For some experiments, AMG was added into the medium together with IL-2 or IL-2+IL-4. Medium with cytokines was changed every day for a further 4 days. The cells were then re-stimulated with 1 μg/ml SIINFEKL (SEQ ID NO:1) in medium containing 2 μM monensin (Calbiochem, La Jolla, Calif.) for 4 hours.

RNA Preparation and Analysis

Total RNA was extracted from 5×10$^6$ differentiated CD8+ T cells using the RNeasy Mini kit (Qiagen, Valencia, Calif.). 1 μg of total RNA was converted into cDNA using iScript cDNA Synthesis kit (Bio-Rad, Hercules, Calif.). Quantitative RT-PCR was performed using Cyp11a1 primers and probe obtained from Applied Biosystems (Cat: Mm00490735_m1). Fold-changes were determined using the 2$^{-\Delta\Delta Ct}$ method, with normalization to expression of mouse GAPDH.

ELISA for Pregnenolone Measurements

CD8+ T cells generated in the presence of IL-2, IL-2+IL-4, IL-2+AMG, or IL-2+IL-4+AMG were cultured in 6-well plates at 5×10$^6$/ml for 24 hours. Supernatants were collected. Pregnenolone levels were measured using the Pregnenolone ELISA kit (ALPCO Diagnostics, Salem, N.H.).

Immunoblot Analysis

CD8+ T cells (5×10$^6$) were lysed with RIPA buffer containing Hale™ protease and phosphatase inhibitor cocktail (Thermo Scientific, Rockford, Ill.) on ice for 30 minutes. Samples were run by sodium dodecyl sulfate polyacrylamide gel electrophoresis (SDS-PAGE) and transferred to nitrocellulose membranes. The membranes were blocked using buffer containing 2% BSA and 0.5% sodium azide in TBST for 1 hour and incubated with rabbit polyclonal Cyp11a1 antibody (Lifespan Biosciences, Seattle, Wash.) overnight at 4° C. Horseradish peroxidase-conjugated anti-rabbit IgG (GE Healthcare, UK) was used to detect Cyp11a1 protein. Mouse monoclonal anti-β-actin antibody (Sigma, St. Louis, Mo.) was used as internal control. Immunoreactive bands of Western blottings were quantified by densitometric quantification of autoradiographs using Image J (NIMH, Bethesda, Md.), and expressed as relative Cyp11a1 normalized by β-actin.

CD8+ T Cell Transfection

CD8+ T cells were transfected with a construct encoding an shRNA specific for mouse Cyp11a1 in the pGFP-V-RS vector (Origene, Rockville, Md.) using an Amaxa mouse T cell nucleofector kit (Amaxa/Lonza, Cologne, Germany). A sequence encoding a non-effective 29-mer scrambled shRNA in the GFP-V-RS vector was used as control. Transfection was performed as directed by the manufacturer (Amaxa/Lonza, Cologne, Germany) using 4 μg of plasmid and Nucleofector Program X-001. Twenty-four hours after transfection, cells were harvested and stimulated with SIINFEKL (1 μg/ml) (SEQ ID NO:1) in medium containing 2 μM monensin for 4 hours and then harvested for flow cytometric analysis.

Flow Cytometric Analysis

For intracellular staining, 1×10$^6$/ml cells were washed twice with PBS containing 1% BSA, stimulated with 1 μg/ml SIINFEKL in the presence of 2 μM monensin at 37° C. for 4 hours. After fixation with 4% paraformaldehyde (Electron Microscopy Sciences, Hatfield, Pa.) and permeabilization with 0.1% saponin (Sigma, St. Louis, Mo.), cells were washed twice with PBS containing 1% BSA, then incubated with anti-mouse CD16/CD32 (2.4G2) (BD Bioscience, San Jose, Calif.) at 4° C. for 5 minutes, then stained with FITC labeled anti-mouse IFN-γ (XMG 1.2) (eBioscience, San Diego, Calif.) or PerCP-Cy5.5 labeled anti-mouse IFN-β (XMG 1.2) (eBioscience) and PE-labeled anti-mouse IL-13 (eBio13A) (eBioscience). For some experiments, fixed cells were stained with biotin labeled rabbit anti-Cyp11a1/p450 cc polyclonal antibody (Bioss, Woburn, Mass.) followed by PE-Cy5 labeled streptavidin (PE-Cy5-SAv) (eBioscience). Cell staining was monitored on a FACSCalibur (BD Bioscience) and analyzed using Flowjo software (Tree Star, Inc, Ashland, Oreg.).

Secondary Allergen Challenge Model and Adoptive Transfer

The experimental protocol for sensitization and challenge to OVA was as described previously (Oka, H. et al. *Cell. Immunol.* 206, 7-15 (2000); Sundrud, M. S, and Nolan, M. A. *Curr. Opin. Immunol.* 22, 286-292 (2010)), with some modification. CD8-deficient mice were sensitized with 20 μg of OVA (Calbiochem, La Jolla, Calif.) emulsified in 2.25 mg of alum (AlumImuject; Pierce, Rockford, Ill.) on days 0 and 14 by intraperitoneal injection. Mice were challenged with 0.2% OVA for 20 minutes on days 21, 22, and 23 using an ultrasonic nebulizer (model NE-U07; Omron Healthcare, Kyoto, J P). To address the effect of Cyp11a1 inhibitor on CD8+ T cell-mediated AHR, CD8+ T cells (5×10$^6$) generated in medium containing IL-2 or IL-2+AMG were injected into OVA-sensitized CD8-deficient mice intravenously on day 37. Two hours after transfer, mice were challenged (secondary) with 1% OVA for 20 minutes. Airway function was measured and samples were collected on day 38.

Assessment of Airway Function

Airway function was assessed as described previously (Oka, H. et al. *Cell. Immunol.* 206, 7-15 (2000); Sundrud, M. S, and Nolan, M. A. *Curr. Opin. Immunol.* 22, 286-292 (2010)) by measuring changes in airway resistance (RL) in response to increasing doses of inhaled methacholine (Sigma, St. Louis, Mo.). Data were presented as percentage change from the baseline RL values after saline inhalation. Baseline RL values were not significantly different among the various groups.

BAL Analysis

After measurement of AHR, lungs were lavaged via the tracheal tube with 1 ml of HBSS. The supernatants were collected and IL-4, IL-5, and IL-13 (eBioscience, San Diego, Calif.) levels were measured by ELISA as described previously. Total leukocyte numbers were counted and differentiated as described previously (Oka, H. et al. *Cell. Immunol.* 206, 7-15 (2000); Sundrud, M. S, and Nolan, M. A. *Curr. Opin. Immunol.* 22, 286-292 (2010)).

Immunohistochemistry Staining

CD8+ T cells generated in the presence of IL-2 or IL-2+IL-4 were collected on slides. After fixing in 4% paraformaldehyde, the slides were stained with anti-human Cyp11a1 antibody (Abcam, Cambridge, Mass.).

Mouse lungs were isolated and fixed in 10% formalin, then embedded in paraffin and cut into 5-μm thick tissue sections. Sections were stained with periodic acid-Schiff (PAS) and mucus-containing cells were quantitated as previously described (Oka, H. et al. *Cell. Immunol.* 206, 7-15 (2000); Sundrud, M. S, and Nolan, M. A. *Curr. Opin. Immunol.* 22, 286-292 (2010)). For some experiments, lung tissue expression of Cyp11a1 was identified by immunohistochemistry staining using anti-human Cyp11a1 antibody.

Statistical Analysis

All data were representative of at least 3 independent experiments, 4 mice/group. Results were expressed as the mean±SEM. Student's two-tailed t test was used to determine the level of difference between two groups. ANOVA was used to determine the levels of difference among more than 3 groups. Nonparametric analysis using the Mann-Whitney U test or Kruskal-Wallis test was also used to confirm that the statistical differences remained significant even if the underlying distribution was uncertain. The p values for significance were set to 0.05 for all tests.

Example 1

This example demonstrates that Cyp11a1 mRNA, protein levels, and enzymatic activity are increased in CD8+ T cells differentiated in the presence of IL-2+IL-4.

CD8+ T cells were differentiated in vitro in the presence of IL-2 or IL-2+IL-4 (FIG. 1A). Following culture for 6 days, total RNA was extracted, cDNA was prepared and quantitative real-time PCR was performed. As illustrated in FIG. 1B, Cyp11a1 mRNA levels were significantly higher in cells differentiated in the presence of IL-4. Similarly, Cyp11a1 protein levels were elevated in these cells (FIG. 1C) as determined by densitometric quantification of immunoreactive bands on autoradiographs. Cells differentiated in IL-2 alone expressed little Cyp11a1 mRNA or protein. Immunohistochemical analysis for Cyp11a1 also showed a dramatic increase in the numbers of positively stained cells in cultures treated with IL-2+IL-4 compared to IL-2 alone (FIG. 1D).

Figure 2:
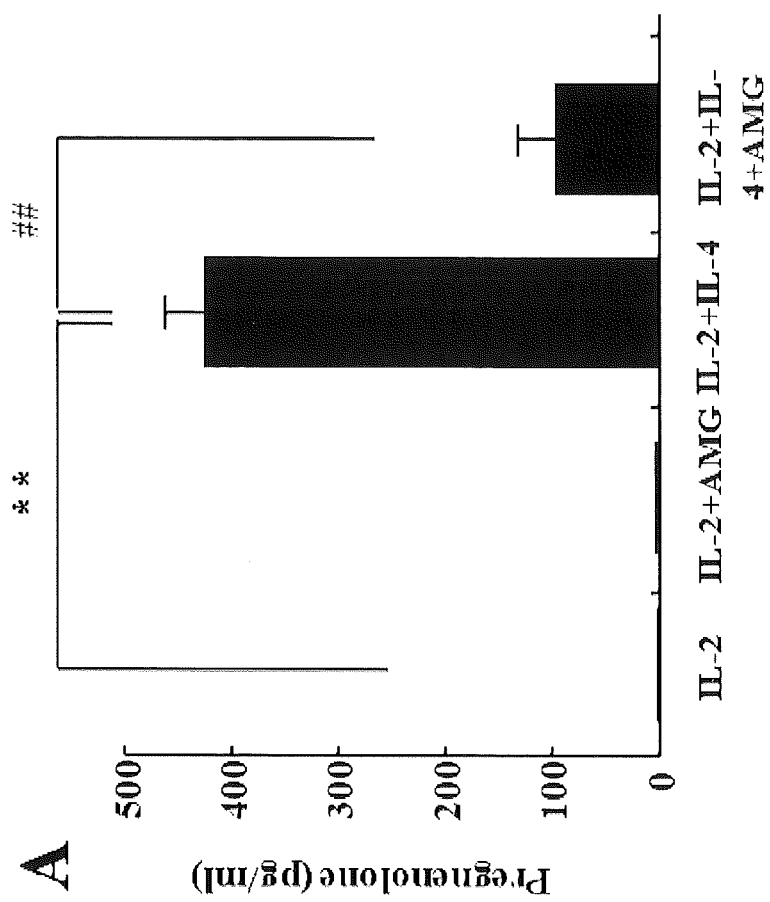
FIGS. 2A-C show Cyp11a1 enzymatic activity regulates the functional conversion of CD8$^+$ T cells from IFN-γ- to IL-13-producing cells. (A) Pregnenolone levels determined by ELISA in supernatants from CD8$^+$ T cells differentiated in IL-2 or IL-2+IL-4 in the presence or absence of AMG (500 μM). $p<0.01$ compared to the IL-2 group. ##$p<0.01$ compared to the IL-2+IL-4 group. (B) Cyp11a1 protein levels detected by immunoblot analysis and densitometry of autoradiographs in CD8$^+$ T cells differentiated in IL-2 or IL-2+IL-4 with 500 μM AMG. $p<0.01$ compared to the IL-2 group. ##$p<0.01$ compared to the IL-2+SIINFEKL group. (C) Flow cytometric analysis of cytokine expression in CD8$^+$ T cells differentiated in IL-2 or IL-2+IL-4 and treatment with different concentrations of AMG. Data are from at least 7 independent experiments.
Figure 2:
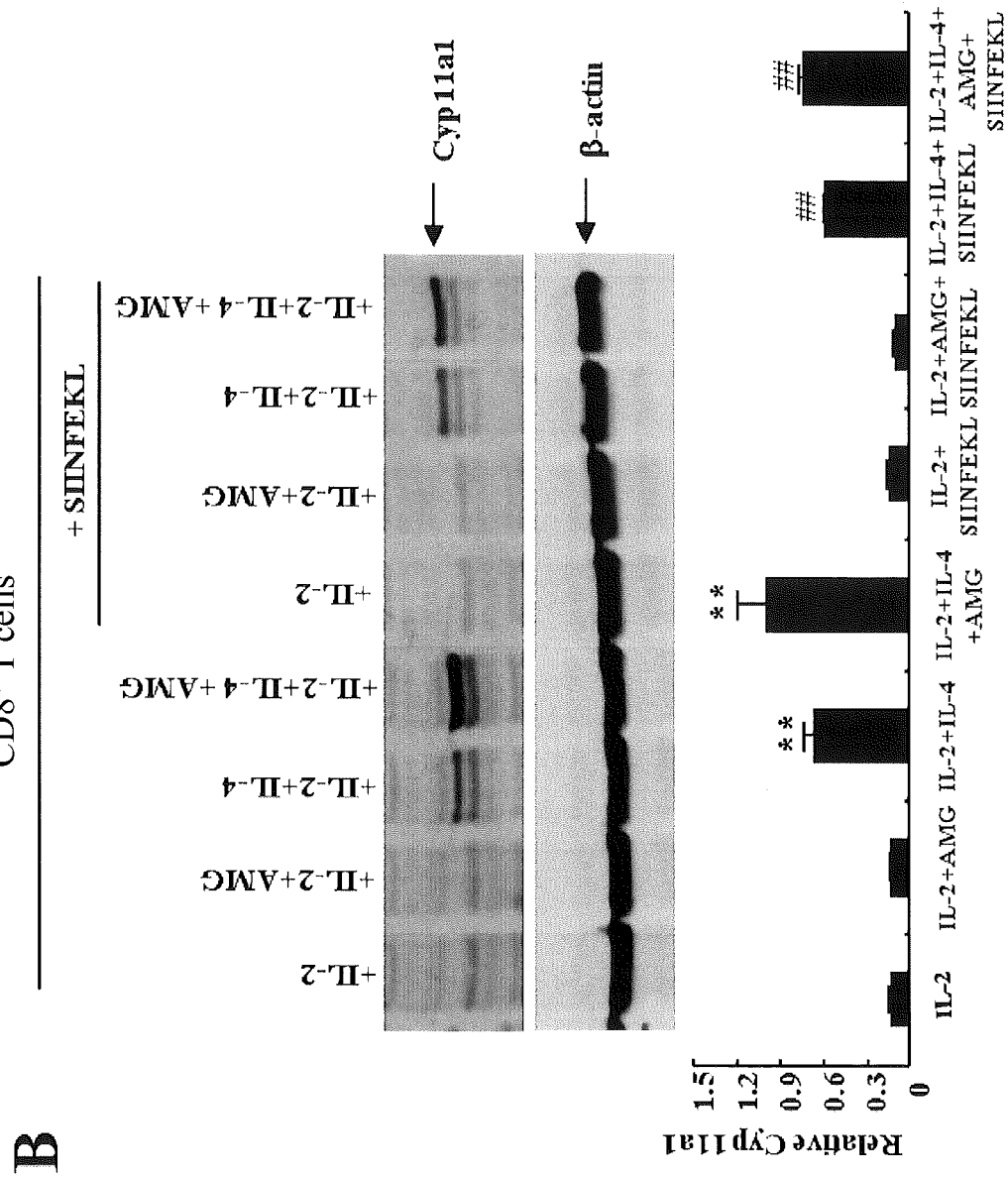
Figure 2:
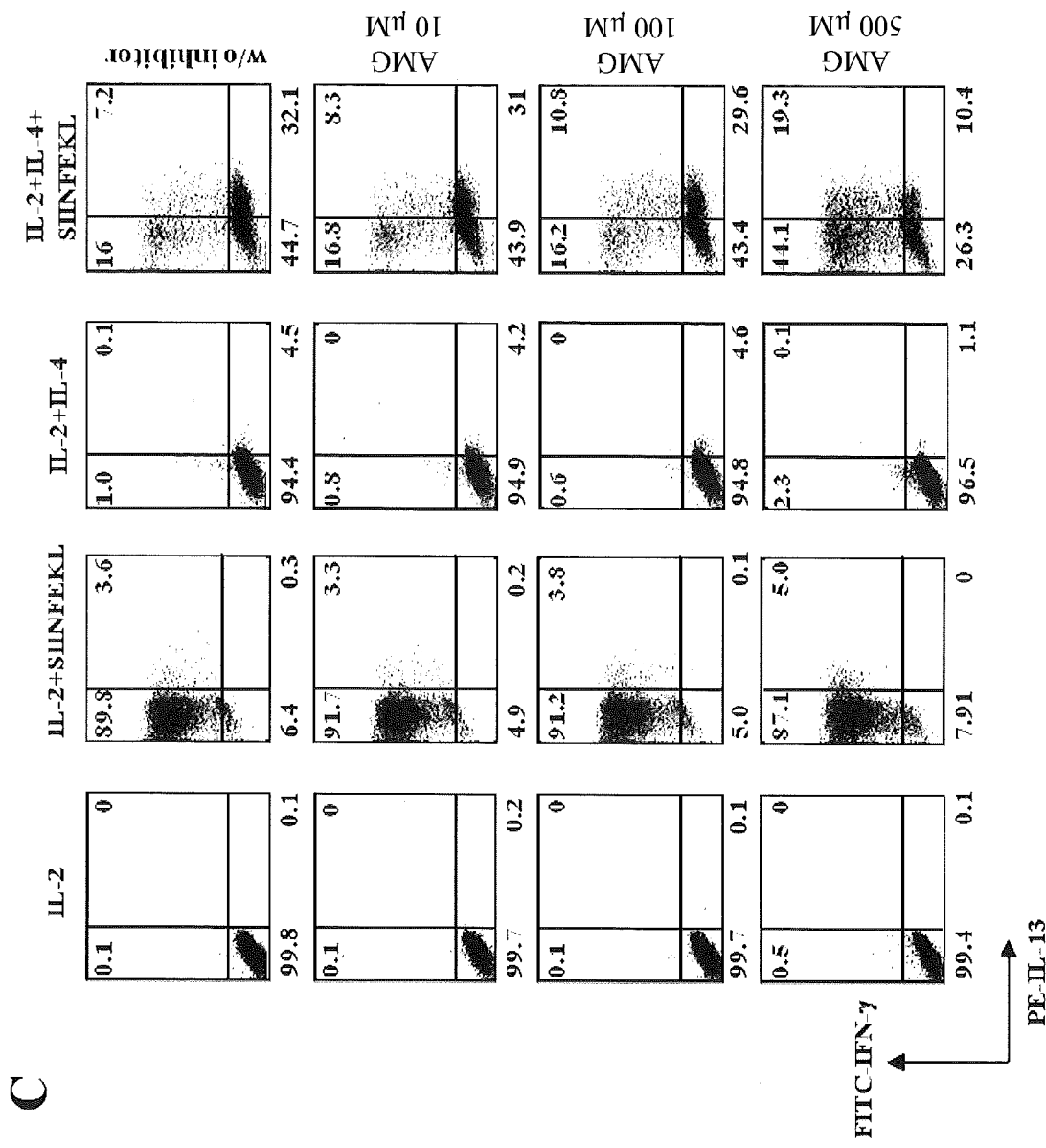

The enzymatic activity of Cyp11a1 was assessed using an ELISA assay for detection of pregnenolone levels in cell culture supernatants (Kim, C. J. et al. *J. Clin. Endocrinol. Metab.* 93, 696-702 (2008)). As shown in FIG. 2A, levels of pregnenolone were increased in cultures of cells differentiated in IL-2 alone (1.8±0.5 pg/ml) to 424.8±35.5 pg/ml in the cells differentiated in IL-2+IL-4.

Example 2

This example demonstrates that aminoglutethimide (AMG) inhibits the enzymatic activity of Cyp11a1 without affecting mRNA or protein expression.

AMG is known to inhibit Cyp11a1 enzymatic activity at the initial step of conversion of cholesterol to pregnenolone in tissues such as the adrenals (Rebel, P. et al. *J. Steroid Biochem. Molec. Biol.* 53, 355-360 (1995); Slominski, A. et al. *FEBS J.* 273, 2891-2901 (2006)). In cells differentiated in IL-2+IL-4, addition of AMG decreased pregnenolone levels in cell supernatants from 424.8±35.5 pg/ml to 96.4±35 pg/ml (FIG. 2A). In contrast, the addition of AMG did not prevent IL-4-induced increases in Cyp11a1 protein levels (with or without re-stimulation with SIINFEKL (OVA$_{257-264}$) SEQ ID NO:1) as determined by immunoblot analysis (FIG. 2B). In fact, levels of protein were increased in AMG-treated cells. These data suggested that the changes in pregnenolone levels were restricted to the regulation of Cyp11a1 enzymatic activity and not due to changes in Cyp11a1 protein levels or cell toxicity.

Example 3

This example demonstrates that Cyp11a1 enzymatic activity is essential for the functional conversion of CD8+ T cells from IFN-γ to IL-13 producing cells.

CD8+ T cells differentiated in IL-2 or IL-2+IL-4 were re-stimulated with SIINFEKL (SEQ ID NO:1) and analyzed for cytokine production by flow cytometry. CD8+ T cells differentiated in IL-2 alone were predominantly IFN-γ-producing with almost no IL-13-producing cells. In contrast, CD8+ T cells differentiated in IL-2+IL-4 were predominantly IL-13 producing, with fewer cells producing IFN-γ (FIG. 2C and Table 1). To assess the importance of the enzymatic activity of Cyp11a1 in the functional conversion of CD8+ T cells, the effect of addition of the Cyp11a1 enzyme inhibitor AMG on these events was determined. CD8+ T cells were differentiated in IL-2 or IL-2+IL-4 and activated through the TCR with SIINFEKL (SEQ ID NO:1) in the presence or absence of AMG When CD8+ T cells were cultured with SIINFEKL (SEQ ID NO:1) and IL-2+IL-4 in the presence of AMG, there was a dramatic dose-dependent decrease in the percentage of IL-13-positive cells and an increase in IFN-γ-positive cells (FIG. 2C). In the presence of 500 μM AMG, the percentage of IL-13-single-positive cells decreased from 35.7±8.2% to 14.7±8.9% and the percentage of IFN-γ-single-positive cells increased from 14.5±5.8% to 42.4±11.5%; the percentage of IFN-γ- and IL-13-double-positive cells increased slightly from 8.8±2.3% to 14.7±5.5% (FIG. 2C and Table 1). The increased numbers of IFN-γ-positive cells in the cultures indicated that the drug did not have an overall suppressive or toxic effect and that Cyp11a1 enzymatic activity was indeed required for the functional conversion of the cells to IL-13 production.

TABLE 1

IFN-γ and IL-13 expression in CD8+ T cells differentiated in IL-2 or IL-2+IL-4 in the presence or absence of AMG

| | IL-2 | IL-2+ AMG | IL-2+ SIINFEKL | IL-2+ AMG+ SIINFEKL | IL-2+ IL-4 | IL-2+ IL-4+ AMG | IL-2+ IL-4+ SIINFEKL | IL-2+ IL-4+ AMG+ SIINFEKL |
|---|---|---|---|---|---|---|---|---|
| INF-γ single positive cells | 0.2 +/− 0.1 | 0.2 +/− 0.1 | 85.6 +/− 3.8 | 78.3 +/− 8.3 | 0.6 +/− 0.2 | 0.9 +/− 0.5 | 14.5 +/− 5.8 | 42.4 +/− 11.5 ** |
| IL-13 single positive cells | 0.2 +/− 0.1 | 0.4 +/− 0.2 | 0.5 +/− 0.5 | 0.1 +/− 0.1 | 3.4 +/− 1.4 | 2.3 +/− 1.5 | 35.7 +/− 8.2 | 14.7 +/− 8.9 ** |
| INF-γ$^+$IL13$^+$ Double positive cells | 0 | 0 | 5.2 +/− 1.1 | 9.0 +/− 2.7 | 0 | 0.1 | 8.8 +/− 2.3 | 14.7 +/− 5.5 |

Intracellular staining of IFN-γ and IL-13 in CD8$^+$ T cells with or without 1 μg/ml SIINFEKL or 500 μM AMG treatment. Data (mean +/− SEM) showing % positive cells were from at least 4 independent experiments. **$p < 0.01$ compard to the IL-2+IL-4+ SIINFEKL group.

Example 4

This example demonstrates that silencing of Cyp11a1 with an shRNA can prevent conversion of CD8$^+$ T cells from IFN-γ to IL-13-producing cells.

Figure 3:
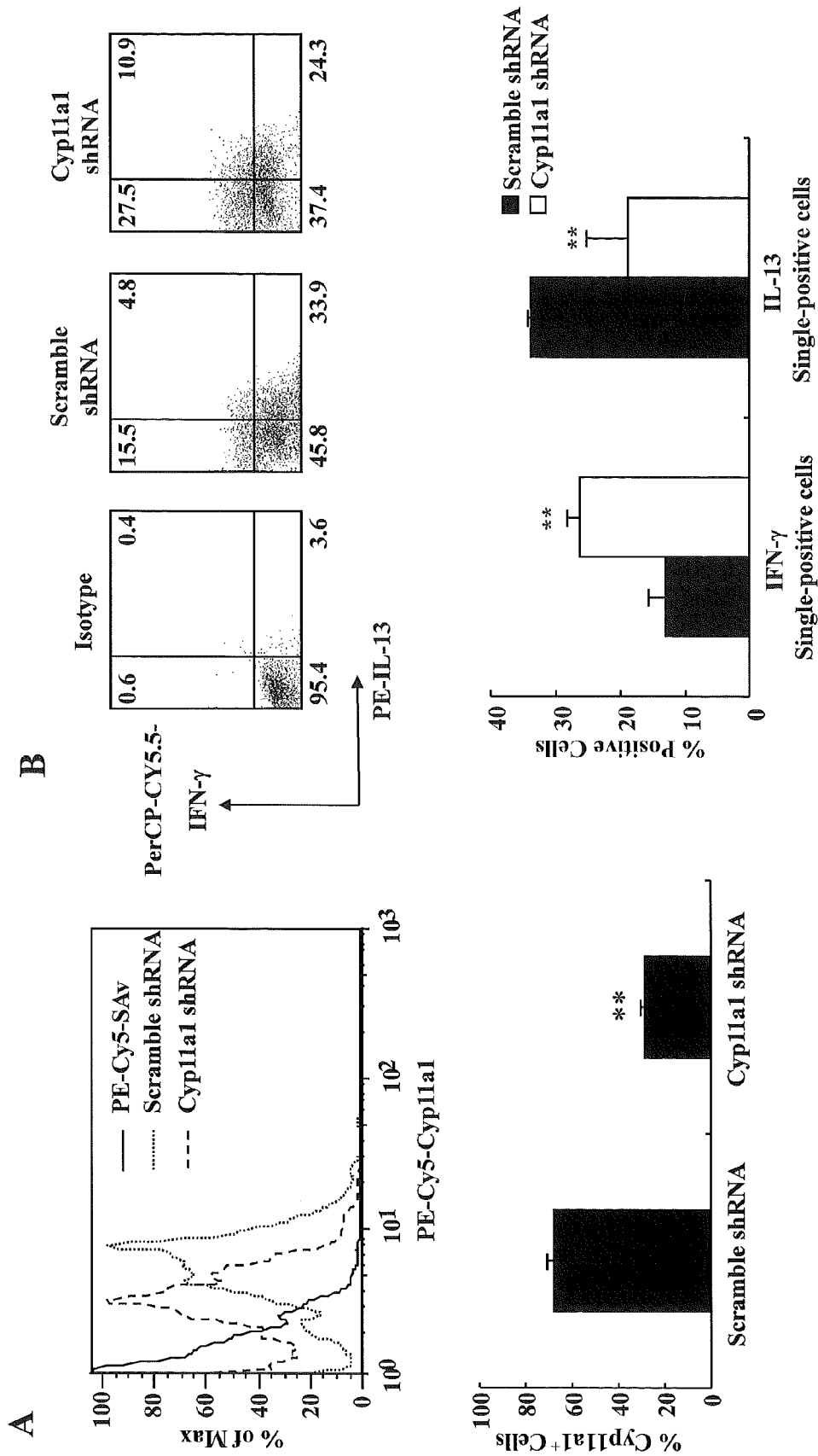
FIGS. 3A-B show that a short hairpin RNA (shRNA) specific for Cyp11a1 prevents the conversion of CD8$^+$ T cells from IFN-γ- to IL-13-producing cells. (A) Representative flow cytometric analysis of Cyp11a1 expression after transfection with plasmids encoding a Cyp11a1 shRNA or a scrambled control shRNA. For quantitative analysis of Cyp11a1-positive cells, data are from at least 4 independent experiments. p<0.01 compared to scramble shRNA group. (B) Representative flow cytometric analysis of cytokine expression in CD8+ T cells after transfection. For quantitative analysis of Cyp11a1-positive cells, data are from at least 3 independent experiments. p<0.01 compared to scramble shRNA group.

To further assess the requirement for Cyp11a1 activity, CD8$^+$ T cells differentiated in the presence of IL-2+IL-4 were transfected with a green fluorescent protein (GFP)-encoding vector containing an shRNA construct specific for mouse Cyp11a1. A non-effective 29-mer scrambled shRNA in the vector was used as control. Forty-eight hours after transfection, the cells were stimulated with SIINFEKL (SEQ ID NO:1) for 4 hours. Flow cytometric analysis for GFP indicated that there were 40.2±0.7% and 43.6±1.9% GFP-positive cells following transfection of Cyp11a1-specific or scrambled shRNA, respectively. Among the GFP-positive cells, 67.8±2.8% of cells receiving the control shRNA was positive for Cyp11a1 and this was significantly reduced to 28.8±1.2% by the Cyp11a1-specific shRNA (FIG. 3A). After transfection of the plasmid encoding the Cyp11a1-specific shRNA, the percentage of IFN-γ-single-positive cells increased to 26.3±1.7% compared to 13±2.7% in cells transfected with the scrambled shRNA; in parallel, the percentage of IL-13-single-positive cells decreased from 33.7±0.6% (scrambled shRNA) to 18.7±6.3% in cells transfected with the Cyp11a1-specific shRNA. The percentage of IFN-γ- and IL-13-double-positive cells increased slightly from 5.9±1.2% to 11±0.1% (FIG. 3B). These results demonstrated that reduction of Cyp11a1 in IL-2+IL-4 differentiated cells resulted in increased IFN-γ and decreased IL-13 expression.

Example 5

This example demonstrates that lineage-specific transcription factor levels in CD8+ T cells are unaffected by AMG treatment.

Figure 4:
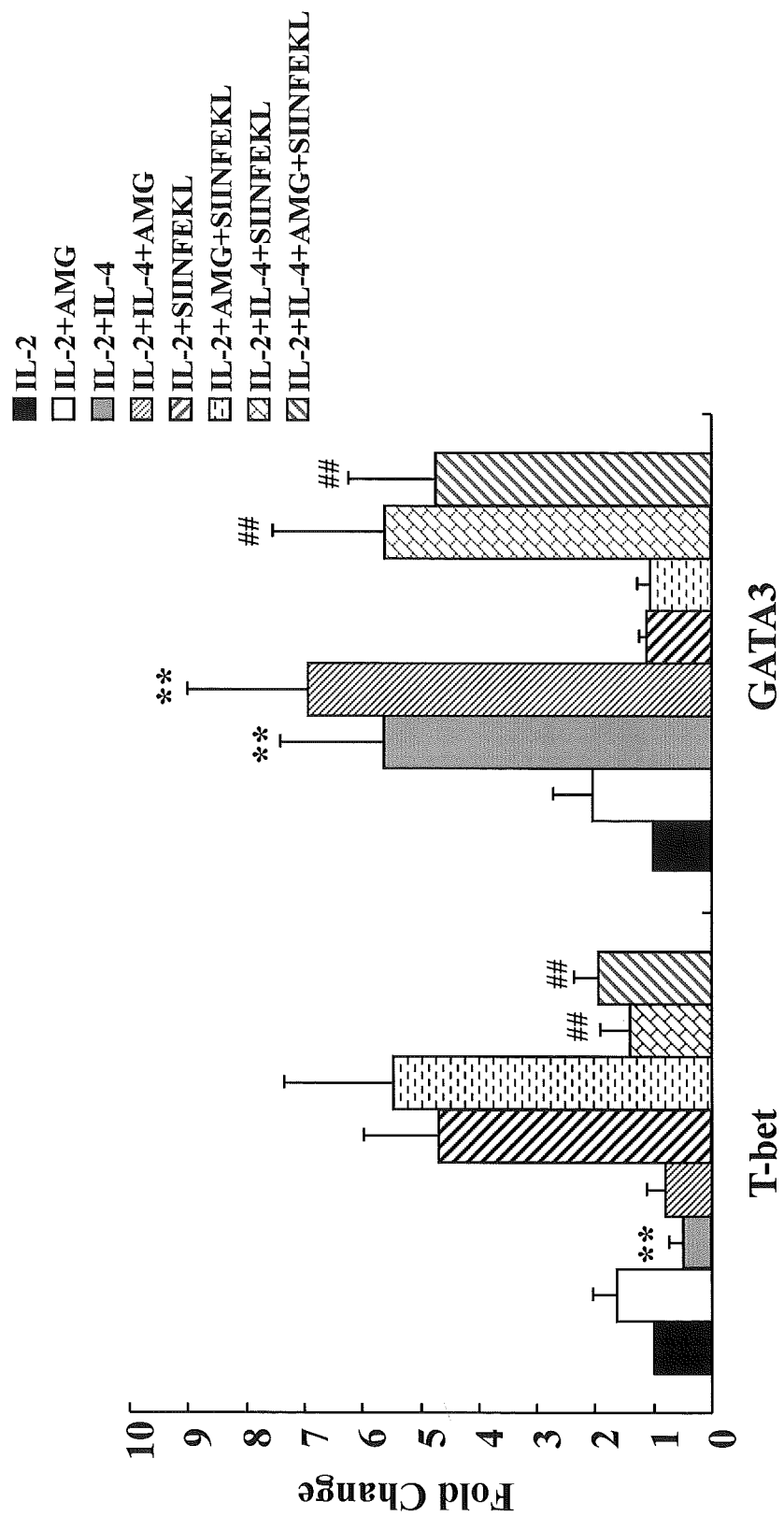
FIG. 4 shows the lineage specific transcription factor expression in CD8+ T cells. T-bet and GATA3 expression detected by quantitative RT-PCR in CD8+ T cells differentiated in IL-2 or IL-2+IL-4 with or without SIINFEKL in the presence or absence of 500 µM AMG Data (mean±SEM) are from at least 8 independent experiments. **p<0.01 compared to the IL-2 group. ##p<0.01 compared to the IL-2+ SIINFEKL group.

The major transcription factors regulating expression of IFN-γ and IL-13 in T cells are T-bet and GATA3, respectively (Oka, H. et al. Cell. Immunol. 206, 7-15 (2000); Sundrud, M. S. and Nolan, M. A. Curr. Opin. Immunol. 22, 286-292 (2010)). Since Cyp11a1 appeared to play an important role in controlling IFN-γ and IL-13 production in CD8$^+$ T cells, the relationship of Cyp11a1 and lineage-specific transcription factor expression was examined. In cells differentiated in IL-2+IL-4, T-bet levels were decreased and GATA3 levels were increased compared to cells differentiated in IL-2 alone (FIG. 4). However, unlike cytokine levels, there were no significant differences observed in cells untreated or treated with AMG. These data suggested that Cyp11a1 enzymatic activity exhibited regulatory activity downstream of the expression of these lineage-specific transcription factors.

Example 6

This example demonstrates that adoptive transfer of AMG-treated CD8+ cells fails to restore CD8+ T cell-mediated AHR and inflammation in vivo.

The inventors have demonstrated that CD8-deficient mice develop a low level of AHR and eosinophilic inflammation compared to WT mice following sensitization and challenge, but that adoptive transfer of primed CD8$^+$ T cells differentiated in IL-2 can restore AHR, eosinophilia, and goblet cell metaplasia, suggesting in vivo conversion (Amsen, D. et al. Curr. Opin. Immunol. 21, 153-160 (2009); Miyahara, N. et al. Nature Med. 10, 865-869 (2004); Ohnishi, H. et al. J. Allergy Clin. Immunol. 121, 864-871 (2008)). This was confirmed following recovery of transferred CD8$^+$ T cells from the lung and demonstrating their ability to produce IL-13 (National Asthma Education and Prevention Program (National Heart Lung and Blood Institute) Third Expert Panel on the Management of Asthma. National Center for Biotechnology Information (U.S.). Expert panel report 3 guidelines for the diagnosis and management of asthma. Bethesda, Md.: National Institutes of Health National Heart Lung and Blood Institute; 2007). As shown in vitro, the in vivo conversion of transferred CD8$^+$ T cells was dependent on IL-4 (Martin, R. J. et al. J. Allergy Clin. Immunol. 119, 73-80 (2007)).

Figure 1:
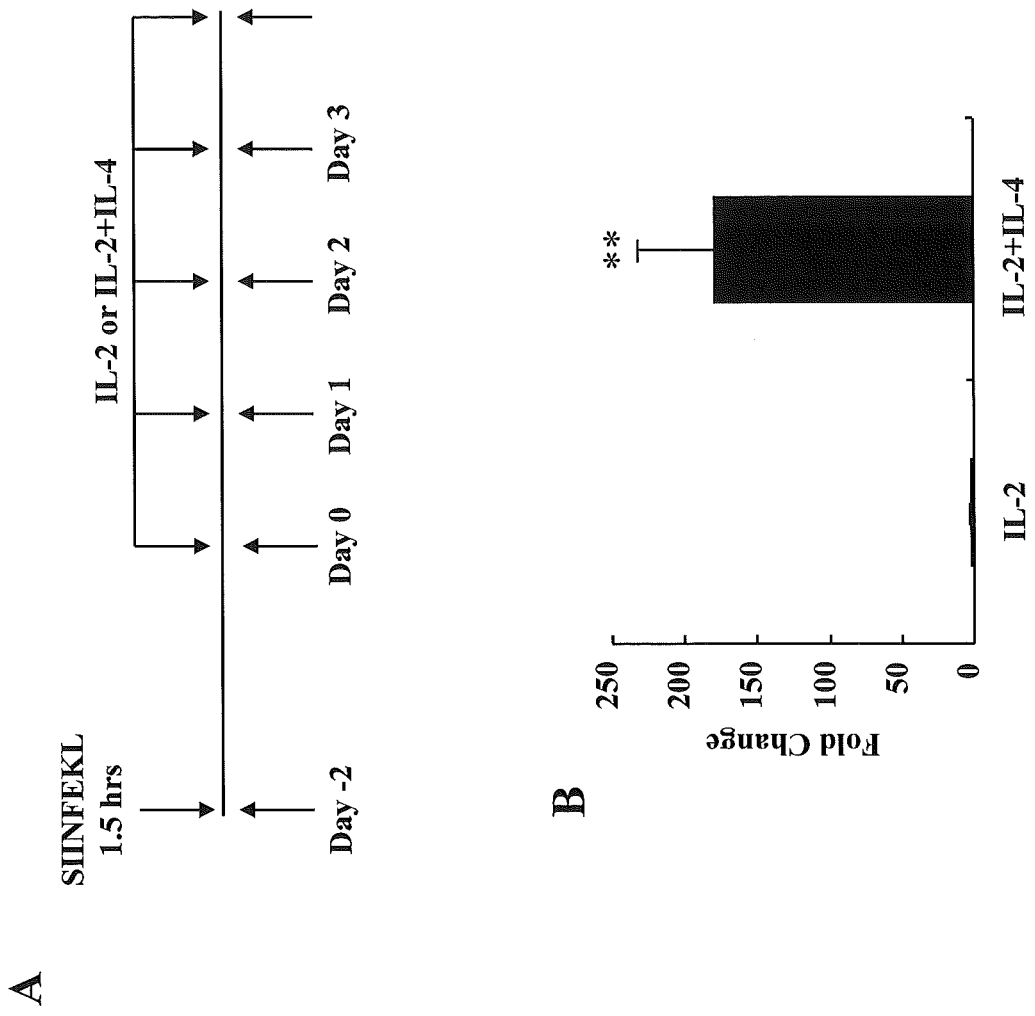
FIGS. 1A-D show Cyp11a1 expression in CD8$^+$ T cells generated in the presence of IL-2 or IL-2+IL-4. (A) Protocol for differentiation of CD8$^+$ T cells in IL-2 or IL-2+IL-4 in vitro. (B) Cyp11a1 mRNA expression as detected by quantitative RT-PCR in CD8$^+$ T cells differentiated in IL-2 or IL-2+IL-4. (C) Cyp11a1 protein levels as detected by immunoblot analysis and densitometry of autoradiographs in CD8$^+$ T cells differentiated in IL-2 or IL-2+IL-4. (D) Immunohistochemical staining for Cyp11a1 in CD8$^+$ T cells differentiated in IL-2 or IL-2+IL-4 in vitro (×200). Quantitative analysis was performed by counting Cyp11a1-positive cells under the microscope. Data (mean±SEM) are from at least 3 independent experiments. **$p<0.01$ compared to the IL-2 group.
Figure 1:
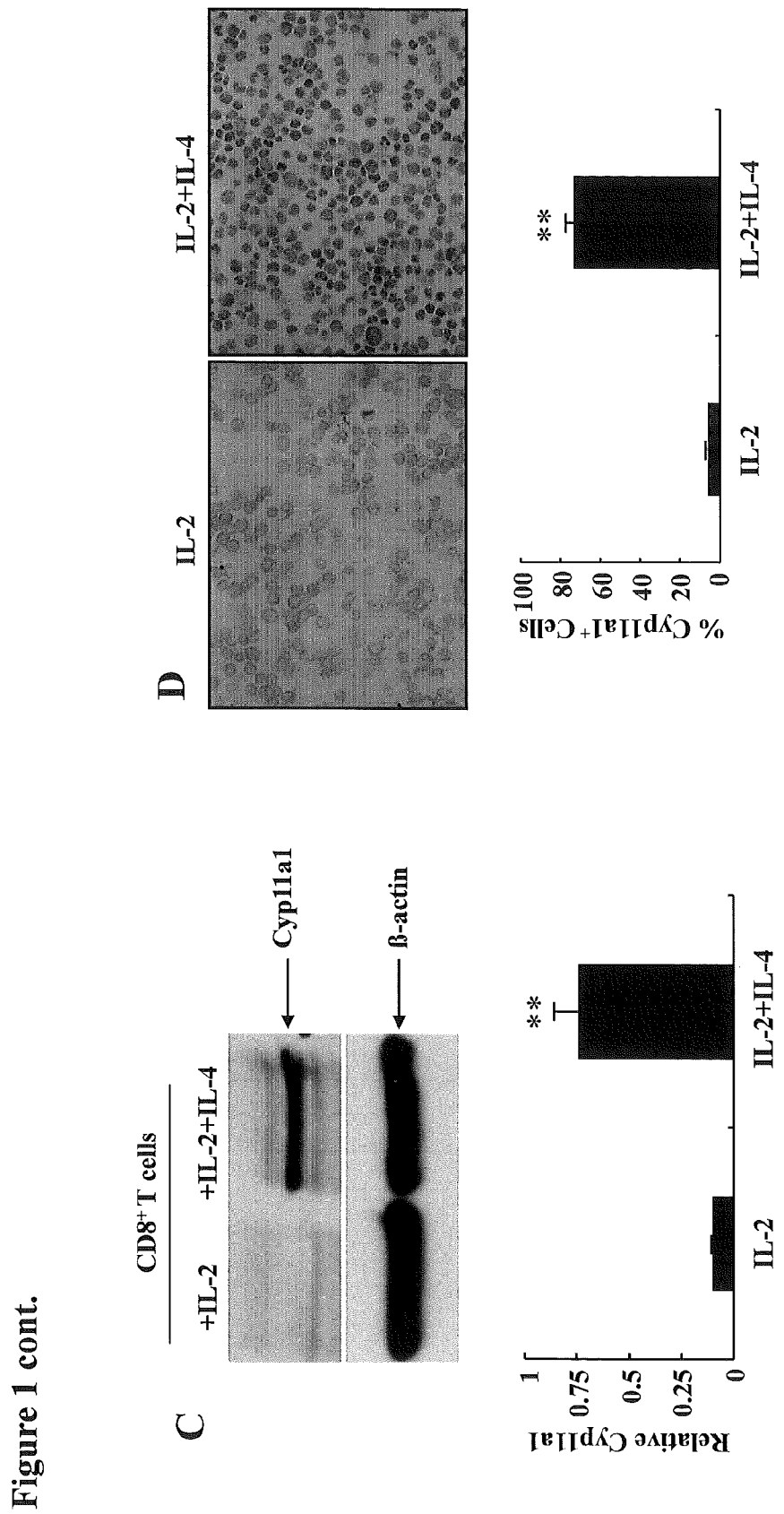
Figure 5:
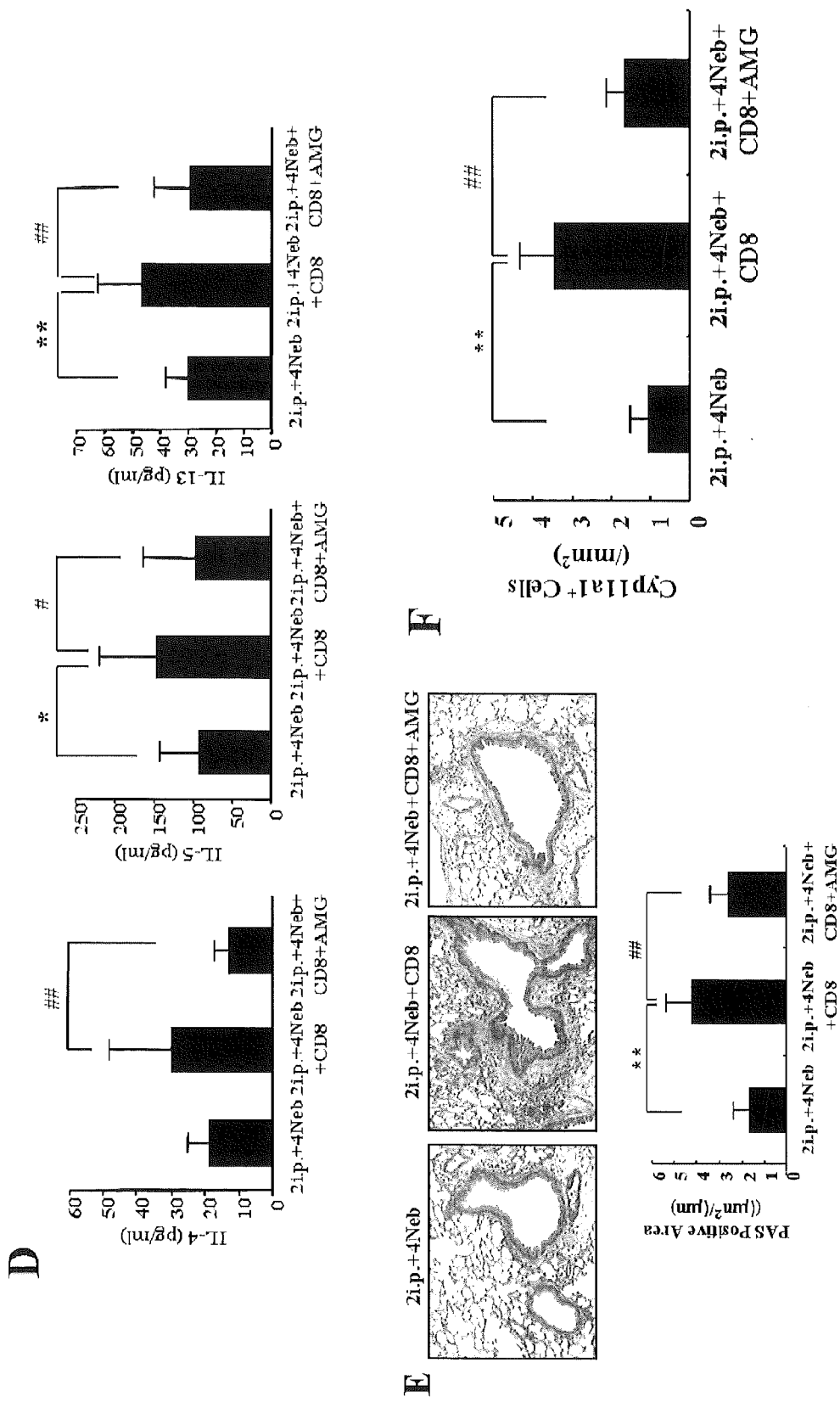
FIGS. 5A-F show the treatment of CD8-deficient recipients with CD8+ T cells differentiated in IL-2 and AMG (500 µM) fails to restore AHR and inflammation. (A) Experimental protocol. (B) Changes in airway resistance (RL). (C) Cell composition in BAL fluid. (D) Cytokine levels in BAL fluid. (E) Representative photomicrographs of lung histology (×200). Quantitative analysis of goblet cells was as described in Materials and Methods. (F) Quantitation of Cyp11a1-positive cells in the lung. Data (mean±SEM) were at least 6-10 mice. *p<0.05, **p<0.01 compared to secondary challenged CD8-deficient recipients. #p<0.05, ##p<0.01 compared to secondary challenged CD8-deficient recipients of 5×10$^6$ IL-2-differentiated CD8+ T cells.

Since AMG prevented IL-4-induced functional conversion of CD8$^+$ T cells from IFN-γ to IL-13 producers in vitro, the inventors determined if this treatment would attenuate restoration of lung allergic responses in vivo. Initial studies determined that the effects of AMG on CD8$^+$ T cell conversion, as demonstrated in FIG. 2C, could be detected for up to forty-eight hours before the cells recovered. Therefore, to ensure that the time frame for the in vivo experiments was consistent with the duration of AMG-mediated inhibition of Cyp11a1 enzyme activity, a secondary challenge model was used which shortens the time interval between cell transfer and assay (FIG. 5A). Transfer of IL-2 differentiated CD8$^+$ T cells into sensitized and challenged CD8-deficient recipients followed by secondary allergen challenge fully restored all lung allergic responses (FIGS. 5B and 5C). In contrast, transfer of CD8$^+$ T cells differentiated in IL-2 in the presence of AMG failed to restore AHR or airway inflammation (FIGS. 5B and 5C). Levels of IL-4, IL-5, and IL-13 were significantly lower in the bronchoalveolar lavage (BAL) fluid of mice which received AMG-treated CD8$^+$ T cells compared to untreated cells (FIG. 5D). Lung sections were processed for histology and analyzed by PAS staining. The results showed that recipients of CD8$^+$ T cells pretreated with AMG had less inflammation and significantly decreased numbers of PAS$^+$ mucus-containing goblet cells compared to those which received CD8$^+$ T cells that had been differentiated in the presence of IL-2 without the enzyme inhibitor (FIG. 5E). Immunohistochemical analysis for Cyp11a1 protein expression in the lung sections was also performed (FIG. 5F and Supplemental FIG. 1). The number of positively-stained cells was significantly increased after adoptive transfer of CD8$^+$ T cells differentiated in IL-2 into sensitized and challenged recipients whereas few Cyp11a1-positive cells were detected in recipients of AMG-treated cells, similar to numbers seen in sensitized and challenged recipients that received no transferred cells.

Examples 7-11 below demonstrate Cyp11a1 enzyme activity in peanut-induced intestinal allergy. In addition, the inventors demonstrate for the first time, the essential role of this enzyme in the full development of intestinal allergic responses and that the inhibition of the enzymatic activity of Cyp11a1 attenuates CD4$^+$ Th2 and Th17 differentiation and cytokine production.

Materials and Methods for Examples 7-11 Described Below

Mice

Five- to 6-week-old female Balb/c wild-type (WT) mice were purchased from the Harlan Laboratory (Indianapolis, Ind.). All studies were conducted under a protocol approved by the Institutional Animal Care and Use Committee of National Jewish Health.

Preparation of Peanut Protein

Crude peanut extract (PE) was prepared from defatted raw flours (Golden Peanut Company, Alpharetta, Ga.) as previously described (E1). Briefly, the flour (1:10, wt/vol) was extracted in 10×PBS overnight at 4° C. After centrifugation at 30,000 g for 60 minutes, the supernatant was filter-sterilized, measured for protein concentration using the BCA method (Pierce, Rockford, Ill.), and stored as aliquots at −20° C. Endotoxin levels in PE solutions were less than 0.1 EU/ml as assessed by a Chromogenic LAL endotoxin assay kit (GeneScript, Piscataway, N.J.).

Sensitization and Intragastric Challenge

The experimental protocol for sensitization and challenge to peanut was previously described (Wang, M., et al. *J. Allergy Clin. Immunol.* 126, 306-316 (2010).

Cyp11a1 Inhibitor Treatment In Vivo and In Vitro

Aminoglutethimide (AMG) was obtained from Sigma (St. Louis, Mo.). PE sensitized and challenged mice received different doses (0-20 mg/kg) of the inhibitor by average, based on doses previously reported (Oka, H., et al. *Cell. Immunol.* 206, 7-15 (2000)) and are described as follows.

AMG was dissolved in 1 M hydrogen chloride and diluted with saline for in vivo studies or diluted with RPMI medium for in vitro study. The final concentration of 1 M hydrogen chloride was less than 1% and 0.05% for in vivo and in vitro, respectively. PE sensitized and challenged mice received different doses (5, 10, 20 mg/kg) of the Cyp11a1 enzyme inhibitor (PE/PE/AMG) by means of gavage using a 22-gauge feeding needle (Fisher Scientific) twice a day during the peanut challenge phase. Controls included PE sensitized and challenged but vehicle (saline) treated (PE/PE/vehicle), or sham sensitized but PE challenged and vehicle-treated (PBS/PE/vehicle) mice.

Assessment of Peanut Intestinal Sensitivity Reactions

Clinical symptoms were evaluated as previously reported (Payne, A. H. *Biol. Reprod.* 42, 399-404 (1990)) and are described in the paragraph below.

Anaphylactic symptoms were evaluated 30 minutes after the oral challenge, as previously reported (Li, X. M., et al. *J. Allergy Clin. Immunol.* 106:150-158 (2000)). Briefly, 0: no symptoms; 1: scratching and rubbing around the nose and head; 2: puffiness around the eyes and mouth, diarrhea, pilar erecti, reduced activity, and/or decreased activity with increased respiratory rate; 3: wheezing, labored respiration, and cyanosis around the mouth and the tail; 4: no activity after prodding or tremor and convulsion; and 5: death. Scoring of symptoms was performed in a blinded manner by an independent observer.

Histology

The jejunum was processed and stained with periodic acid-Schiff (PAS) and chloroacetate esterase for detection of mucosal mucus-containing cells and mast cells respectively, as previously described (Wang, M., et al. *J. Allergy Clin. Immunol.* 126, 306-316 (2010); Tomkinson, A., et al. *Am. J. Respir. Crit. Care Med.* 163, 721-730 (2001)). Numbers of mucosal cells expressing Cyp11a1 were identified by immunohistochemical (IHC) staining using anti-human Cyp11a1 antibody (Abcam, Cambridge, Mass.).

Cytokines Levels in Cell Culture

Levels of IL-4, IL-13, IL-17A, and IFN-γ in cell culture supernatants were measured by ELISA (eBioscience, San Diego, Calif.) as described by the manufacturer.

Measurement of Peanut-Specific Antibody

Serum peanut-specific IgE, IgG1, and IgG2a levels were measured by ELISA, as described previously (Payne, A. H. *Biol. Reprod.* 42, 399-404 (1990)).

Histamine Levels in Plasma

Levels of histamine in plasma were measured using an enzyme immunoassay histamine kit (Beckman Coulter, Fullerton, Calif.), as described by the manufacturer. The concentration of histamine was calculated from a standard curve provided by the manufacturer.

Pregnenolone Levels in Serum and Cell Culture Supernatants

Pregnenolone levels in serum and cell culture supernatants were measured by ELISA (ALPCO Diagnostics, Salem, N.H.), as described by the manufacturer.

T-Cell Differentiation In Vitro

Differentiation of Th1, Th2, or Th17 cells was performed as previously described (40, 41) and is described in the following paragraph.

Differentiation of Th1, Th2, or Th17 cells was performed as previously described with minor changes (Ashino, S., et al. *Intl. Immunol.* 22:503-513 (2010)). CD4$^+$CD45RB$^+$ T cells were isolated from naive TCR-transgenic mice (OT II mice) spleen using a cell sorter (MoFlo XDP, Beckman Coulter). In the presence of mitomycin-C-treated spleen cells, 5 μg/ml $OVA_{323-339}$ peptide, and the inhibitor AMG (400 μm), isolated naive CD4 T cells were cultured with rmIL-2 (10 ng/ml, R/D Systems), rmIL-12 (10 ng/ml, Peprotech), rmIFN-γ (5 ng/ml, Peprotech), and anti-IL-4 mAbs (10 μg/ml, eBioscience) to induce Th1 cell differentiation; with rmIL-2 (10 ng/ml, R/D Systems), rmIL-4 (5 ng/ml, Peprotech), and anti-IFN-γ mAb (10 μg/ml, eBioscience) for differentiation of Th2 cells; and with rhIL-6 (50 ng/ml, Perotech), rhTGF-β (2 ng/ml, Peprotech), rmIL-23 (10 ng/ml, Peprotech), anti-IL-4 mAb (10 μg/ml, eBioscience), and anti-IFN-γ mAb (10 μg/ml, eBioscience) for differentiation of Th17 cells. After 6 days of culture, the cells were washed with fresh medium and restimulated with anti-CD3/anti-CD28 for 24 hrs for assay of cytokine production. The cells were collected for quantitative RT-PCR and Western blot. In some experiments (for transduction experiment), the cells were cultured under Th1, Th2, and Th17 polarizing conditions for 5 days as described in Methods.

Western Blot Analysis

Cell lysates were prepared from cultured CD4 T cells as previously described (Ashino, S., et al. *Intl. Immunol.* 22:503-513 (2010)) and in the following paragraph.

Cultured cells were lysed as previously described (Ohnishi, H., et al. *J. Allergy Clin. Immunol.* 121:864-871 (2008)). Lysates were resolved by means of SDS-PAGE and transferred to nitrocellulose membranes. Proteins were detected using antibodies specific for Cyp11a1 (LifeSpan Biosciences. Seattle, Wash.) followed by chemiluminescence detection (GE Healthcare, Little Chalfont, UK).

Quantitative Real-Time PCR

Real-time PCR was performed as previously described (Wang, M., et al. *J. Allergy Clin. Immunol.* 130, 932-944 (2012)) and in the following paragraph.

RNA was extracted from jejunal tissue homogenates or from CD4 T cells cultured in vitro using Trizol (Invitrogen). cDNA was generated using the iScript cDNA synthesis kit (Bio-Rad Laboratories, Hercules, Calif.). Quantitative real-time PCR was performed on the ABI Prism 7300 sequence detection system (Applied Biosystems, Foster City, Calif.). All primers and probes used were purchased as Taqman Gene Expression Assays from Applied Biosystems. Fold change was calculated using the Delta Delta cycle threshold ($\Delta\Delta C_T$) method.

Expression Constructs

The Cyp11a1 shRNA sequence was generated using the Dharmacon siDESIGN center (Thermo Scientific). Cyp11a1 sense 5'-TTCAATAAAGCTGATGAGTATTCAAGAGA-TACTCATCAGCTTTATTGATTTTTTC-3'(SEQ ID NO:2) anti-sense 5'-TCGAGAAAAAATCAATAAAGCTGAT-GAGTATCTCTTGAATACTCATCAGCTTTATTG AA-3' (SEQ ID NO:3). Control firefly luciferase (luc) shRNA was described previously (Musselman, C. A., et al. *Proc. Natl. Acad. Sci. USA* 109, 787-792 (2012)). To construct the shRNA expression vectors, PAGE-purified and phosphorylated oligonucleotides (Integrated DNA Technologies, Coralville, Iowa) encoding Cyp11a1 shRNA were annealed and ligated into a modified pQCXIP vector (Clontech, Mountain View, Calif.) expressing cyan fluorescent protein (CFP) (Musselman, C. A., et al. *Proc. Natl. Acad. Sci. USA* 109, 787-792 (2012)). Plasmid DNA encoding mouse Cyp11a1 and control firefly luciferase were purified using endofree plasmid maxi kit (Qiagen, Valencia, Calif.) and sequenced (Eton Bioscience, San Diego, Calif.).

Retrovirus Production and Transduction

Retrovirus production was performed as previously described (Maier, H., et al. *Nucleic Acids Res.* 31, 5483-5489 (2003)). ΦNX packaging cells were plated on poly-d-lysine-coated 100-mm dishes and cultured overnight to reach 60 to 80% confluency. Cells were co-transfected with the pCL-Eco viral packaging plasmid and plasmid DNA encoding Cyp11a1, or control luc shRNA using Lipofectamine 2000 (Invitrogen, Carlsbad, Calif.) according to the manufacturer's instructions. Two days post-transfection, the virus-containing supernatant was collected and used to transfect cells.

Retroviral transduction of Th2 cells was performed as previously described (Pham, D., et al. *J. Immunol.* 189, 832-840 (2012)). Sorted $CD4^+$ T cells were cultured under Th2 cell differentiation conditions as previously reported (Wang, M., et al. *J. Allergy Clin. Immunol.* 130, 932-944 (2012)). Cells were transduced with retroviruses (control luc shRNA or Cyp11a1 shRNA) by centrifugation in the presence of 8 μg/ml polybrene (Sigma). Cells were expanded and analyzed on day 5.

Cell Sorting and Analysis of Gene Expression

Seventy-two hours after transduction, the cells were collected and labeled with anti-mouse CD4 FITC (eBiosciences). $CFP^+$ $CD4^+$ cells were sorted using a Synergy cell sorter (iCyt). Sorted cells were stimulated with 2 μg/ml anti-CD3/CD28 for quantitative RT-PCR and ELISA. Quantitative RT-PCR and ELISA were performed as described above.

Cell Viability and Growth

Cell viability was determined using the trypan blue dye exclusion assay. Cell growth was determined by counting the number of viable cells.

Statistical Analysis

ANOVA was used to determine the levels of difference between all groups. Comparisons for all pairs utilized the Tukey-Kramer highest significance difference test. P values for significance were set at 0.05. All results were expressed as the means±SEM.

Example 7

This example demonstrates that the expression of Cyp11a1 is increased in the small intestine of peanut sensitized and challenged mice.

Figure 6:
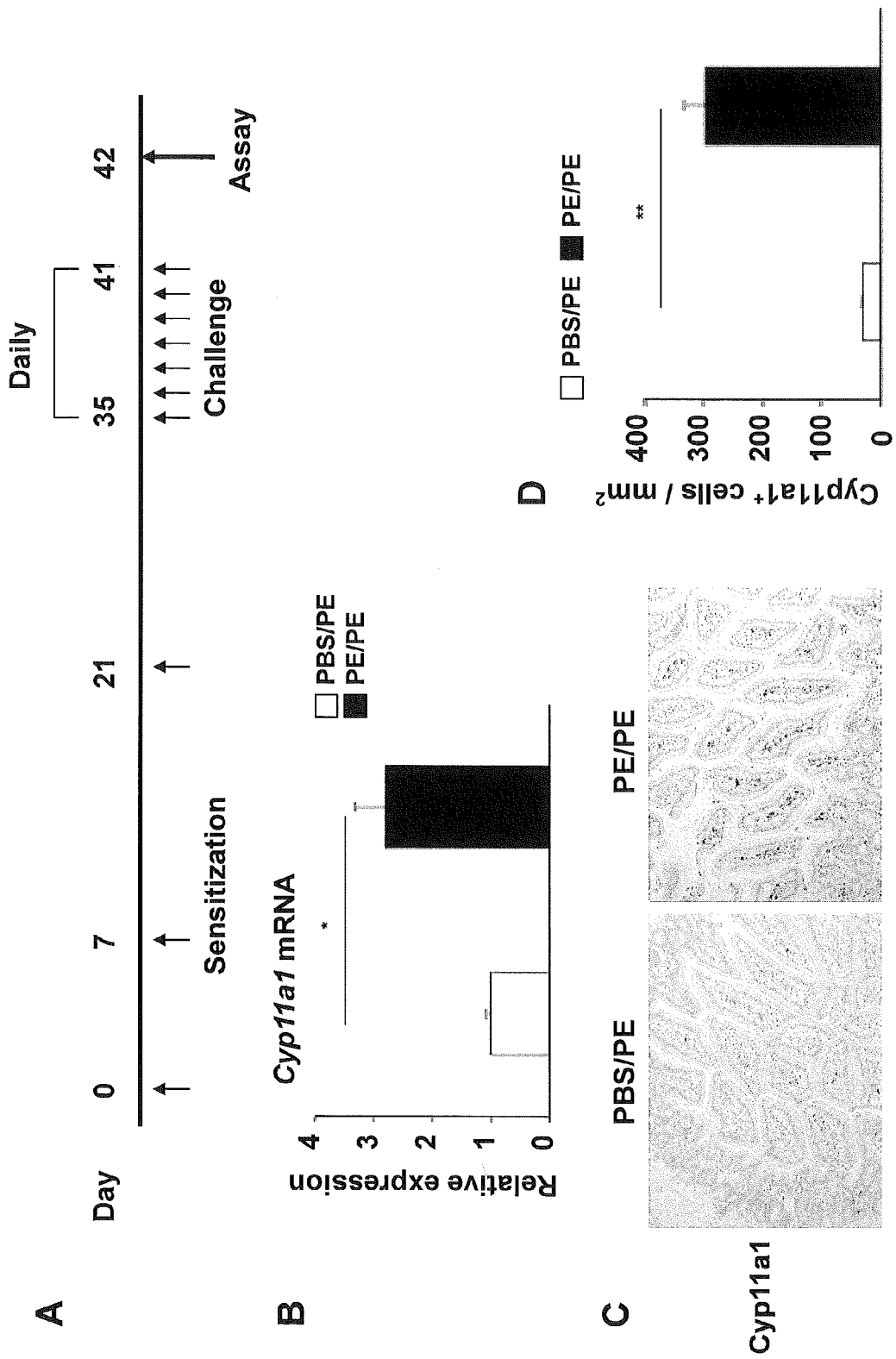
FIGS. 6A-D show Cyp11a1 is expressed in mouse jejunum. (A) Protocol for induction of peanut allergy. (B) Cyp11a1 mRNA expression detected by quantitative RT-PCR in peanut sensitized and challenged vs. sham sensitized and peanut challenged mice. (C) Representative immunohistochemical staining for Cyp11a1 (×200). (D) Quantitation of mucosal Cyp11a1-expressing cells. Results were from 3 independent experiments; each experiment included 4 mice per group (n=12). *P<0.05, **P<0.01. PBS/PE, sham sensitized and peanut challenged; PE/PE, peanut sensitized and challenged.

The expression of Cyp11a1 mRNA and protein in the jejunum of WT Balb/c mice was examined. Following PE sensitization and challenge (FIG. 6A), Cyp11a1 mRNA expression was increased 3-fold in the jejunal homogenates (FIG. 6B). Immunohistochemical staining of jejunal tissue with an antibody specific for Cyp11a1 protein was mainly localized to the lamina propria of the small intestine (FIG. 6C). There were few Cyp11a1-positive cells in the mucosa of the small intestine of sham sensitized mice whereas numbers of Cyp11a1-positive cells were significantly increased in the PE sensitized and challenged mice (FIG. 6D). Thus, Cyp11a1 expression was induced following sensitization and challenge.

Example 8

This example demonstrates that the inhibition of Cyp11a1 attenuates PE-induced allergic responses in vivo.

Figure 7:
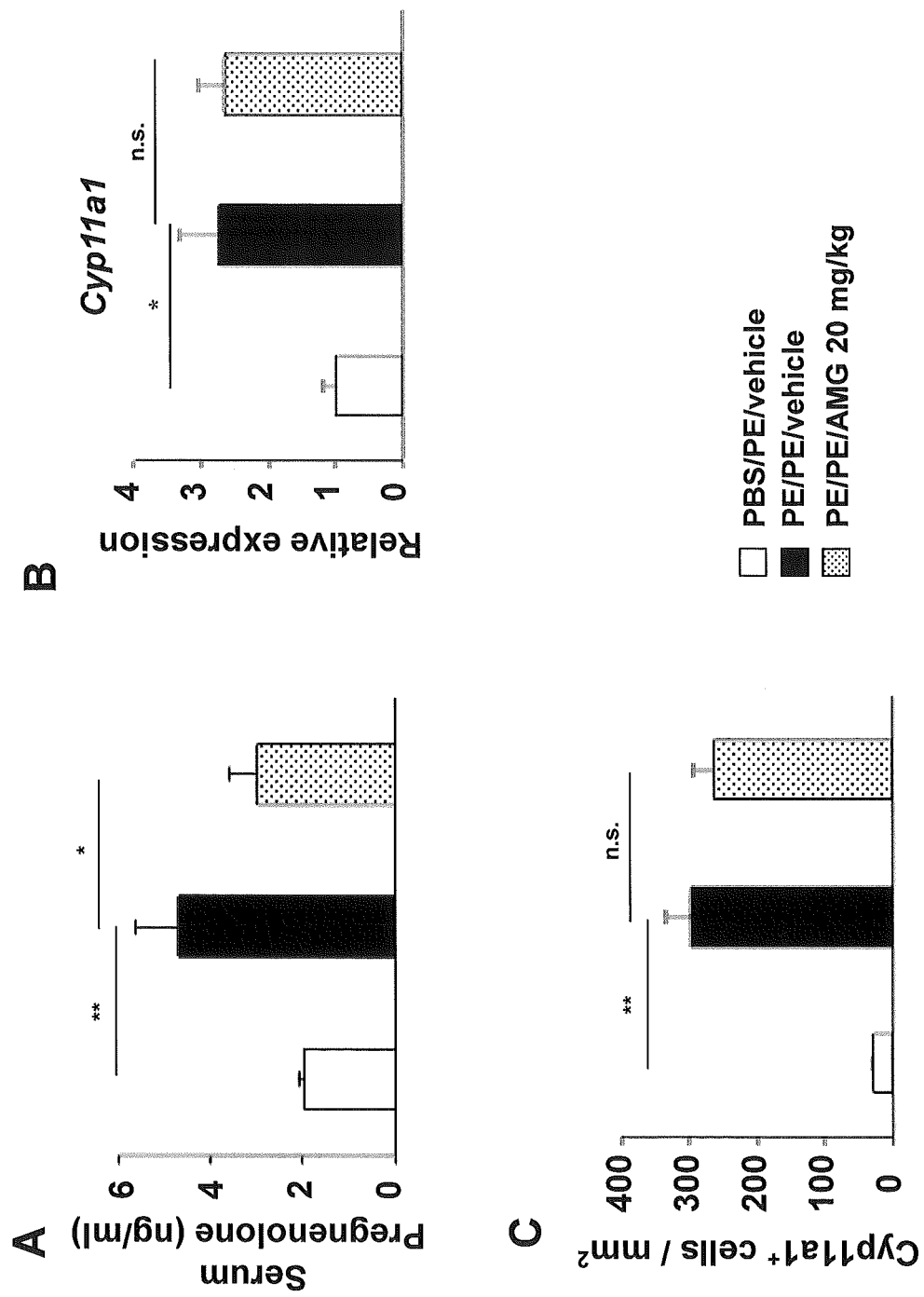
FIGS. 7A-C show the inhibition of Cyp11a1 enzymatic activity does not impact levels of Cyp11a1 protein and mRNA expression in the mouse jejunum. (A) Pregnenolone levels were assessed in serum of mice. (B) Cyp11a1 mRNA expression in jejunum of mice treated with AMG or vehicle. (C) Quantitation of mucosal Cyp11a1-expressing cells. Results were from 3 independent experiments; each experiment included 4 mice per group (n=12). *P<0.05, **P<0.01, n.s. not significant. PBS/PE, sham sensitized and peanut challenged; PE/PE, peanut sensitized and challenged; PE/PE/AMG 20 mg/kg, peanut sensitized and challenged and treated with AMG at dose of 20 mg/kg.

The effects of inhibition of Cyp11a1 enzymatic activation on the induction of peanut allergy using an inhibitor, aminoglutethimide (AMG) was determined AMG is known to block the enzymatic activity of Cyp11a1, thus preventing conversion of cholesterol to pregnenolone (Parajes, S., et al. *J. Clin. Endocrinol. Metab.* 96, E1798-E1806 (2011)). To establish that AMG inhibitory activity was limited to the enzymatic activity, pregnenolone levels in serum were measured following PE sensitization and challenge. As shown in FIG. 7A, levels of pregnenolone were significantly increased in the serum of peanut sensitized and challenged mice (4.69±0.92 ng/ml) compared to sham sensitized but PE challenged mice (1.99±0.11 ng/ml). Levels of pregnenolone were significantly decreased (2.98±0.60 ng/ml) in peanut sensitized and challenged mice following treatment with AMG (20 mg/kg). While PE sensitization and challenge increased Cyp11a1 mRNA and numbers of Cyp11a1-positive cells in the small intestine treatment with AMG (20 mg/kg) did not affect these results (FIGS. 7B, 7C). These data confirm that Cyp11a1 enzymatic activity, in parallel to mRNA and protein expression is induced by peanut sensitization and challenge and that AMG specifically targets the enzymatic activity but not protein expression per se.

Figure 8:
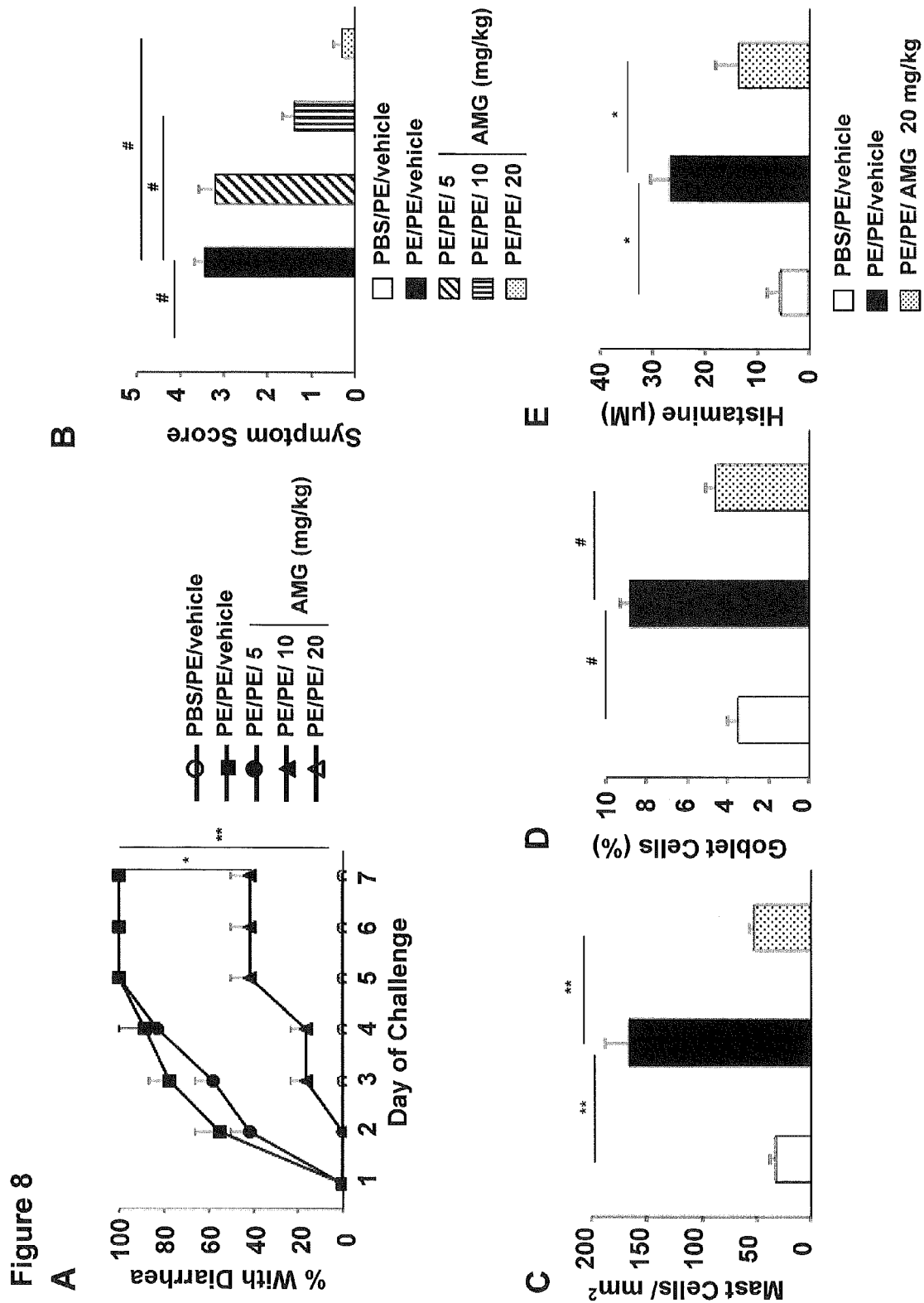
FIGS. 8A-E show the inhibition of Cyp11a1 enzymatic activity in vivo reduces intestinal responses. (A) Kinetics of development of diarrhea after treatment with AMG (Cyp11a1 inhibitor) vs. vehicle. (B) Scores based on the severity of clinical signs were assessed 30 minutes after oral challenge. (C-D) Quantitation of mucosal mast cell and goblet cell numbers in jejunum. (E) Plasma histamine levels were assessed within 30 minutes of the last oral challenge. Results were from 3 independent experiments; each experiment included 4 mice per group. *P<0.05, **P<0.01, #P<0.001.

Administration of the inhibitor to sensitized mice resulted in a dose-dependent inhibitory effect on intestinal allergy induction; 20 mg/kg of the inhibitor fully prevented development of diarrhea and significantly diminished clinical symptom scores in PE sensitized and challenged mice (FIGS. 8A, 8B). Lower doses of the inhibitor (10 mg/kg) partially inhibited diarrhea and symptom scores, whereas 5 mg/kg of the inhibitor had no observed inhibitory effects on diarrhea occurrence or clinical symptoms.

Mast cells are involved in allergic responses (Wang, M., et al. *J. Allergy Clin. Immunol.* 126, 306-316 (2010); Brandt, E. B., et al. *J. Clin. Invest.* 112, 1666-1677 (2003)) and the inventors demonstrated increased numbers of mast cells and mucus-producing goblet cells in the small intestine of PE sensitized and challenged mice (FIGS. 8C, 8D and FIGS. 12 and 13). Mice treated with the Cyp11a1 inhibitor at a dose of 20 mg/kg demonstrated markedly reduced numbers of mast cells as well as mucus-producing goblet cells in the mucosa of the small intestine. To detect mast cell degranulation, plasma levels of histamine were measured within 30 minutes of the last antigen challenge. Challenge of sensitized mice resulted in detection of increased levels of histamine in plasma; following treatment with AMG (20 mg/kg), significantly lower levels of plasma histamine were detected (FIG. 8E).

Figure 14:
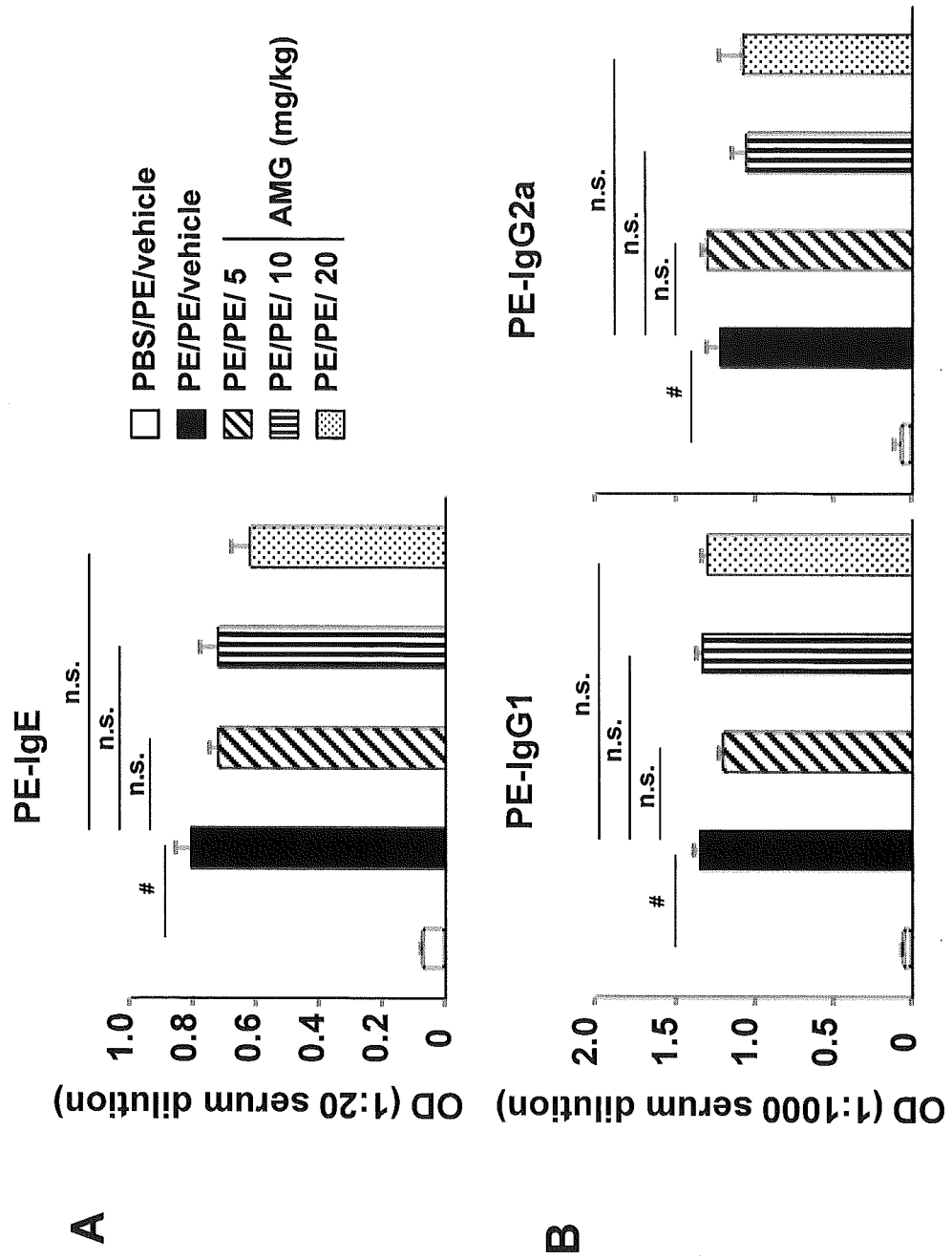
FIG. 14A-B shows the treatment with AMG had no effect on serum immunoglobulin production in peanut sensitized and challenged mice. Serum levels of peanut-specific IgE (FIG. 14A), IgG1 (FIG. 14B), and IgG2a (FIG. 14B) were assessed by ELISA 24 hrs after the last challenge and expressed as optical density of diluted serum as described in Methods. Results were obtained from 3 individual experiments with 4 mice per group. #P<0.001, "n.s." indicates "not significant".

As the inhibitor was administered after sensitization, levels of peanut-specific IgE, IgG1, and IgG2a were unaffected by AMG administration (FIG. 14). Together, these results demonstrate that AMG is a potent inhibitor of the enzymatic activity of Cyp11a1 in vivo without affecting mRNA expression or protein levels of the enzyme. These data demonstrate Cyp11a1's involvement in the triggering of allergic diarrhea and symptoms, intestinal inflammation, and goblet cell metaplasia.

Example 9

This example demonstrates that the inhibition of Cyp11a1 enzymatic activity suppresses Th2 and Th17 cytokine production without impacting the expression of lineage-specific transcription factors in vivo.

Figure 9:
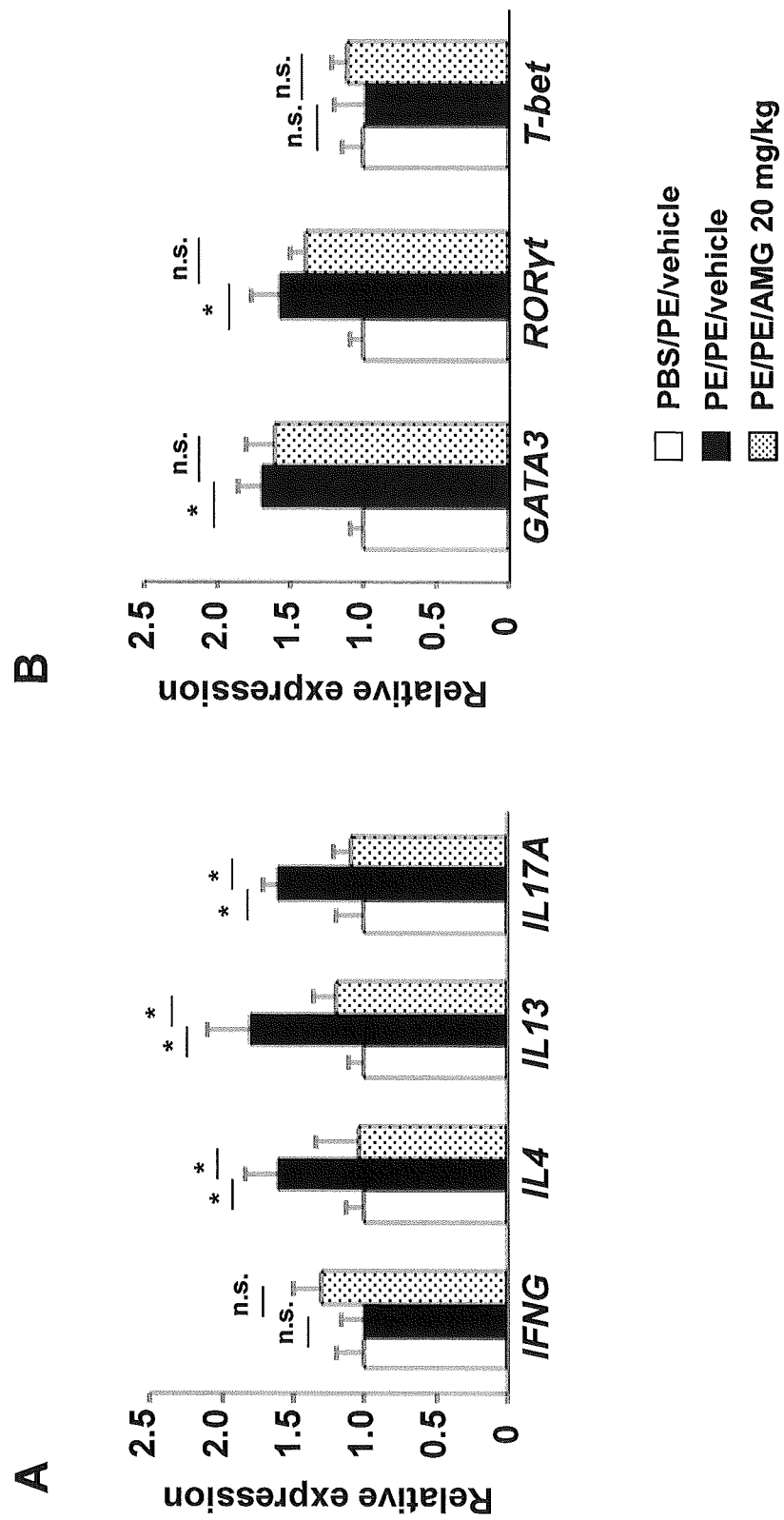
FIGS. 9A-B show the effects of Cyp11a1 inhibition on cytokine and lineage-specific transcription factor expression in the mouse jejunum. (A) IFNG, IL4, IL13, and IL17A mRNA expression in jejunum of mice treated with AMG or vehicle. (B) Th1, Th2, and Th17 transcription factors T-bet, GATA3, and RORγt expression in jejunum of mice treated with AMG or vehicle. Results were from 3 independent experiments (n=12). *P<0.05, **P<0.01, n.s. not significant.

Th2 and Th17 cells have been implicated in the development of allergic disorders, including asthma and food allergy (Wang, M., et al. *J. Allergy Clin. Immunol.* 130, 932-944 (2012); Wills-Karp, M., et al. *Science* 282, 2258-2261 (1998); Corren, J., et al. *N. Engl. J. Med.* 365, 1088-1098 (2011); Kolls, J. K., & Linden, A. *Immunity* 21, 467-476 (2004); Lajoie, S., et al. *Nature Immunol.* 11, 928-935 (2010)). PE sensitization and challenge increased IL4, IL13, and IL17A but not IFNG mRNA expression in the small intestine (FIG. 9A). In parallel, expression of the lineage-specific transcription factors GATA3 and RORγt mRNA were significantly increased in sensitized and challenged mice while levels of T-bet mRNA were not altered (FIG. 9B). After treatment with AMG (20 mg/kg), IL4, IL13, and IL17A mRNA expression were reduced to baseline levels, but expression levels of T-bet, GATA3, or RORγt mRNA were not affected (FIG. 9B), indicating that the effects on cytokine transcription were mediated downstream of these transcription factors. Given that transcription factor expression was still increased in AMG-treated animals, drug toxicity as an explanation of the effects on cytokine expression was eliminated.

Example 10

This example demonstrates that the inhibition of Cyp11a1 enzymatic activity suppresses Th2 and Th17 cell differentiation in vitro without affecting lineage-specific transcription factor or Cyp11a1 expression.

Naive Th cells differentiate into Th1, Th2, and Th17 cells under the control of specific polarizing cytokines and master transcription factors (Zhu, J., et al. *Annu. Rev. Immunol.* 28, 445-489 (2010)). The inventors demonstrate the effect of Cyp11a1 inhibition on Th cell differentiation in vitro. Isolated $CD4^+CD45RB^+$ T cells from spleens of naive TCR transgenic mice (OT II mice) were cultured under Th1, Th2, and Th17 polarizing conditions in the presence or absence of the inhibitor AMG for 6 days and then stimulated with anti-CD3/anti-CD28.

Figure 10:
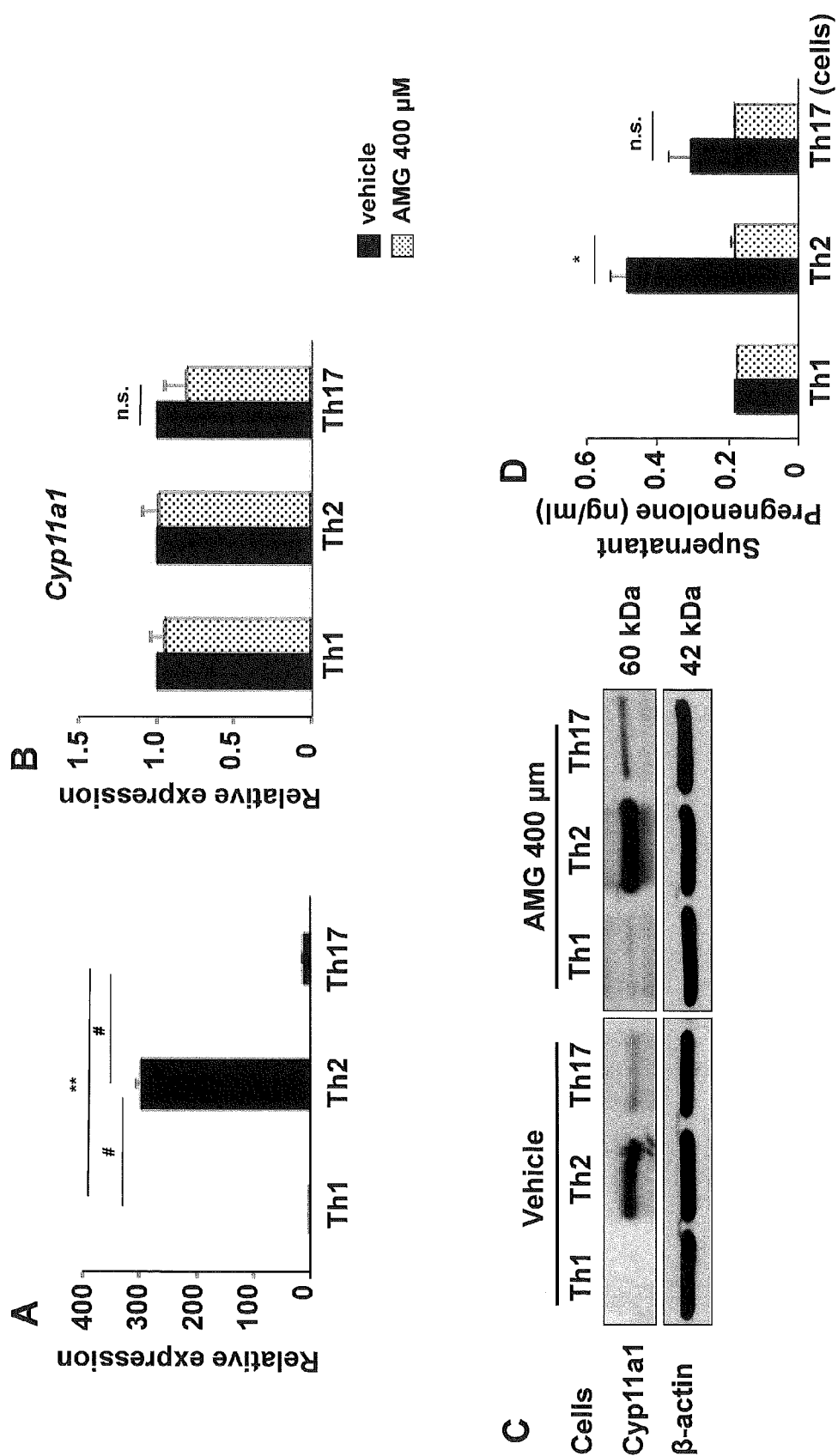
FIGS. 10A-F show the inhibition of Cyp11a1 enzymatic activity suppresses the differentiation of naive CD4 T cells into Th2 and Th17 cells without affecting lineage-specific transcription factor and Cyp11a1 expression. (A). Relative Cyp11a1 expression in naive CD4 T cells differentiated in vitro into Th1, Th2, and Th17 cells from spleen of naive TCR-transgenic mice (OT II mice) determined by real time PCR. (B). Cyp11a1 mRNA expression in polarized CD4 T cells in the presence of AMG or vehicle. (C). Western blot analysis of Cyp11a1 protein in polarized Th1, Th2, or Th17 cells treated with AMG or vehicle. (D). Pregnenolone levels were assessed in supernatants of cultured CD4 T cells under Th1, Th2, and Th17 polarizing conditions. (E) Cytokine levels in supernatants of cultured CD4 T cells treated with inhibitor or vehicle under Th1, Th2, and Th17 polarizing conditions. (F) Th1, Th2, and Th17 cytokine and lineage-specific transcription factor mRNA expression in polarized Th1, Th2, or Th17 cells treated with the inhibitor or vehicle. The data shown are from 3 independent experiments. *P<0.05, **P<0.01, #P<0.001, n.s. not significant.

Addition of AMG to cultured CD4 T cells under Th1, Th2, and Th17 polarizing conditions had significant and distinct effects. In polarized cells, Cyp11a1 mRNA expression was approximately 300-fold higher in Th2 cells compared to Th1 cells and 10-fold higher in Th17 cells compared to Th1 cells (FIG. 10A). The addition of AMG (400 μM) to the cell cultures did not suppress expression levels of Cyp11a1 mRNA or protein in the polarized Th1, Th2, or Th17 cells (FIGS. 10B, 10C). As shown in FIG. 10D, levels of pregnenolone were highest in the culture supernates from polarized Th2 cells, with lower levels released from Th17 cells, followed by release from Th1 cells. Addition of AMG (400 μM) during the polarization of Th cells in vitro significantly decreased levels of pregnenolone in the culture supernates from Th2 cells but not in Th1 cells. Levels in cultures of polarized Th17 cells were also reduced by AMG, but the decreases did not reach statistical significance. These results confirmed the findings that the inhibitory activity of AMG appeared restricted to the enzymatic activity of Cyp11a1 without affecting gene transcription or translation. Further, the data demonstrated the highest levels of Cyp11a1 expression and enzymatic activity in Th2 cells with little to no expression or activity in Th1 cells.

Figure 10E:
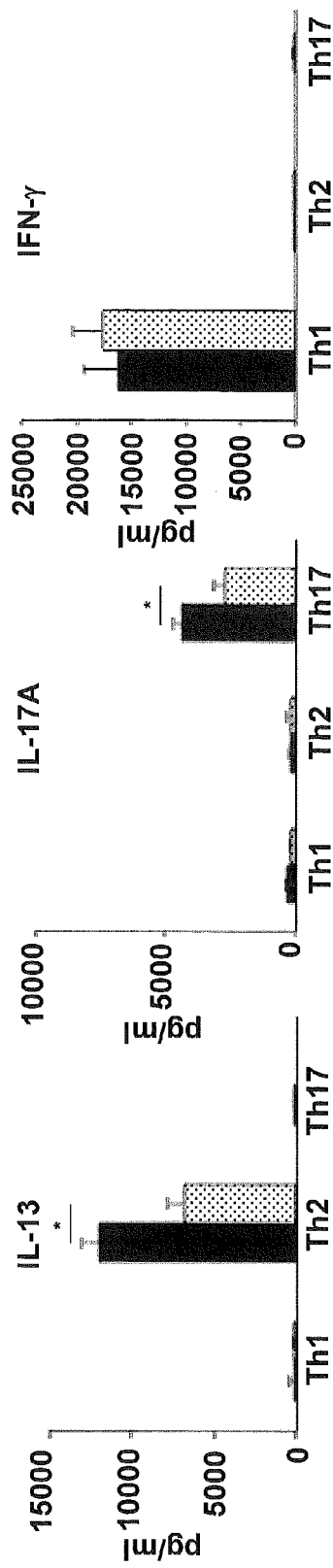
Figure 10F:
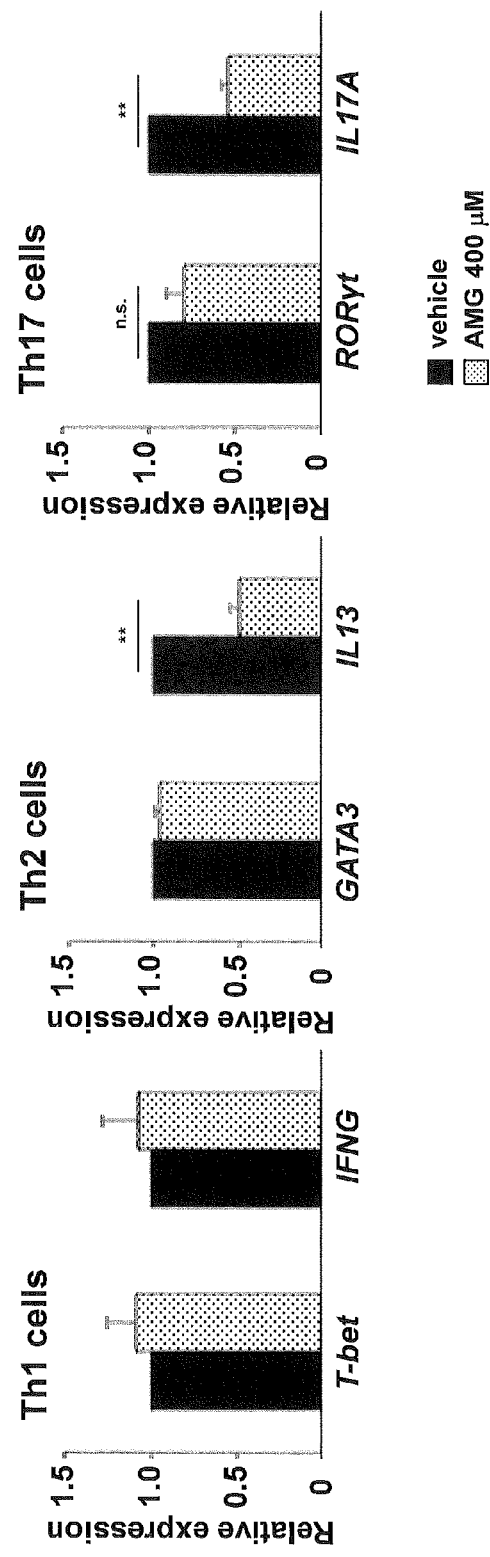

In the culture supernatants of polarized Th2 cell cultures, levels of IL-13 were decreased in the presence of the inhibitor (FIG. 10E); levels of IL-17A were decreased by the inhibitor in polarized Th17 cell cultures, but levels of IFN-γ were not affected by the inhibitor in polarized Th1 cell cultures. In parallel, the inhibitor decreased levels of IL13 and IL17A mRNA in polarized Th2 and Th17 cells, respectively (FIG. 10F) but no significant effects of the inhibitor were detected on IFNG mRNA expression in Th1 cells. Consistent with results from the in vivo studies, the inhibitor (400 μM) did not have any effect on lineage-specific transcription factor mRNA expression, T-bet, GATA3, or RORγt mRNA in polarized Th1, Th2, and Th17 cells, respectively (FIG. 10F).

Example 11

This example demonstrates that shRNA-mediated silencing of Cyp11a1 reduces Th2 cytokine expression.

Figure 11:
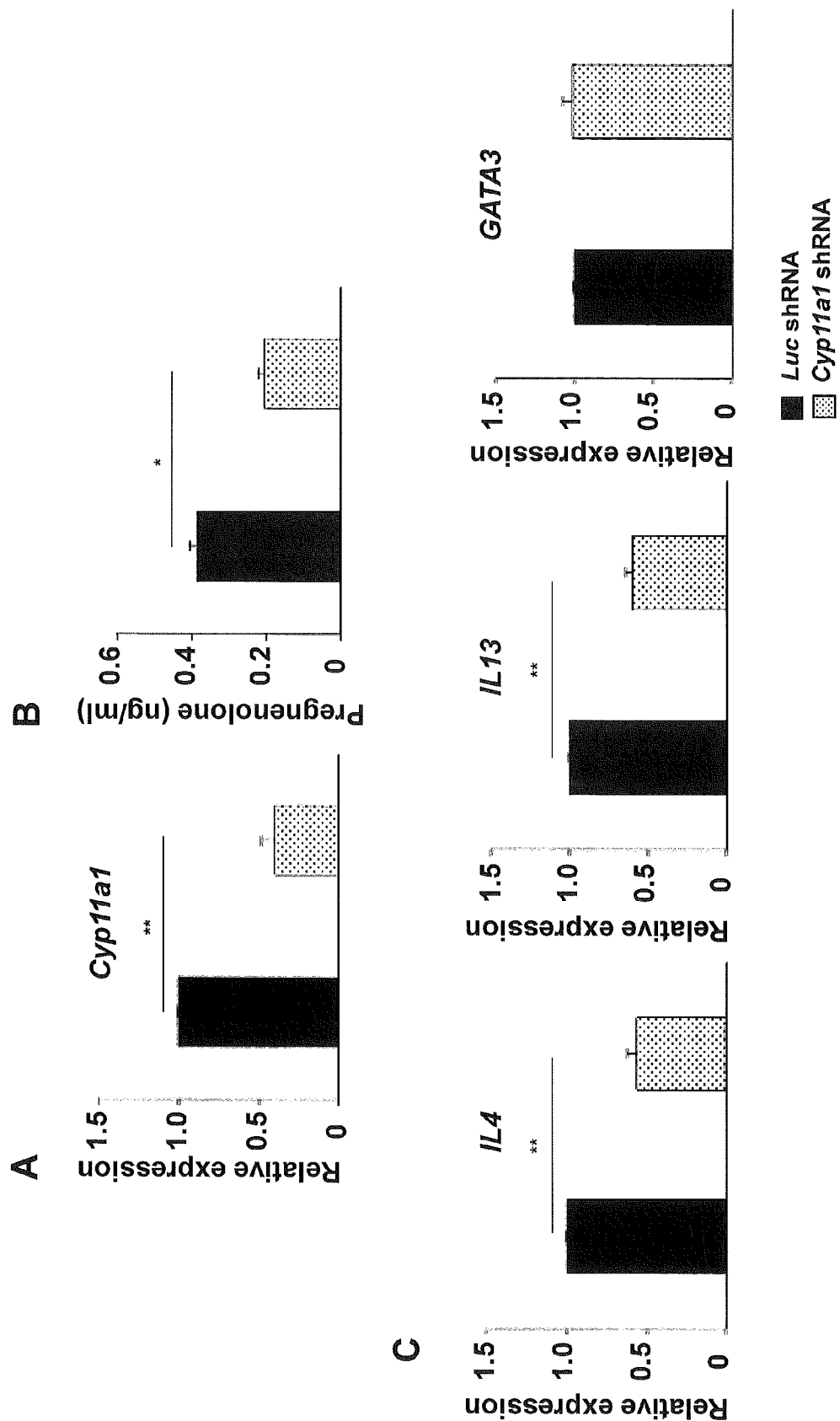
FIGS. 11A-D shows shRNA-mediated silencing of Cyp11a1 regulates levels of IL-13 without affecting levels of GATA3 transcripts in Th2 T cells. (A) Cyp11a1 mRNA expression in shRNA-transduced Th2 cells. (B) Pregnenolone levels were assessed in supernatants of cultured Th2 cells transduced with Cyp11a1 or luc shRNA. (C) Levels of IL4, IL13, and GATA3 mRNA expression in cultured Th2 cells transduced with Cyp11a1 or luc shRNA. (D) Levels of IL-4 and IL-13 in supernatants of cultured Th2 cells transduced with Cyp11a1 or luc shRNA. Results were from 3 independent experiments. *P<0.05, **P<0.01.
Figure 12:
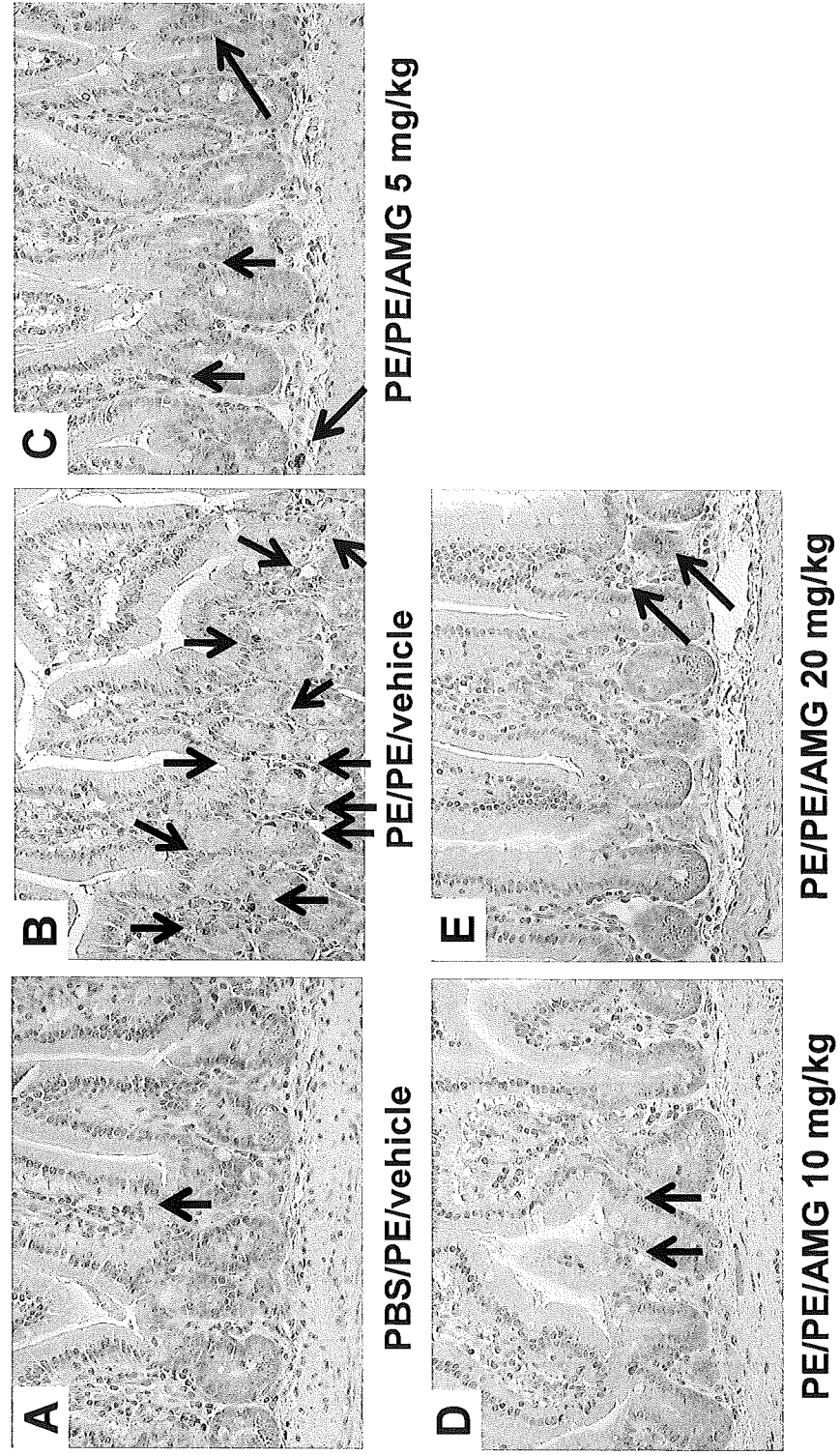
FIGS. 12A-E shows the decreased mast cell infiltration in the intestinal wall of PE/PE mice treated with AMG. Intestinal mucosa mast cells were quantified in jejunum using chloroacetate esterase staining. Representative sections of (A) PBS/PE/vehicle mice; (B) PE/PE/vehicle mice; (C) PE/PE/AMG (5 mg/kg) mice; (D) PE/PE/AMG (10 mg/kg) mice; and (E) PE/PE/AMG (20 mg/kg) mice. Magnification ×400.
Figure 13:
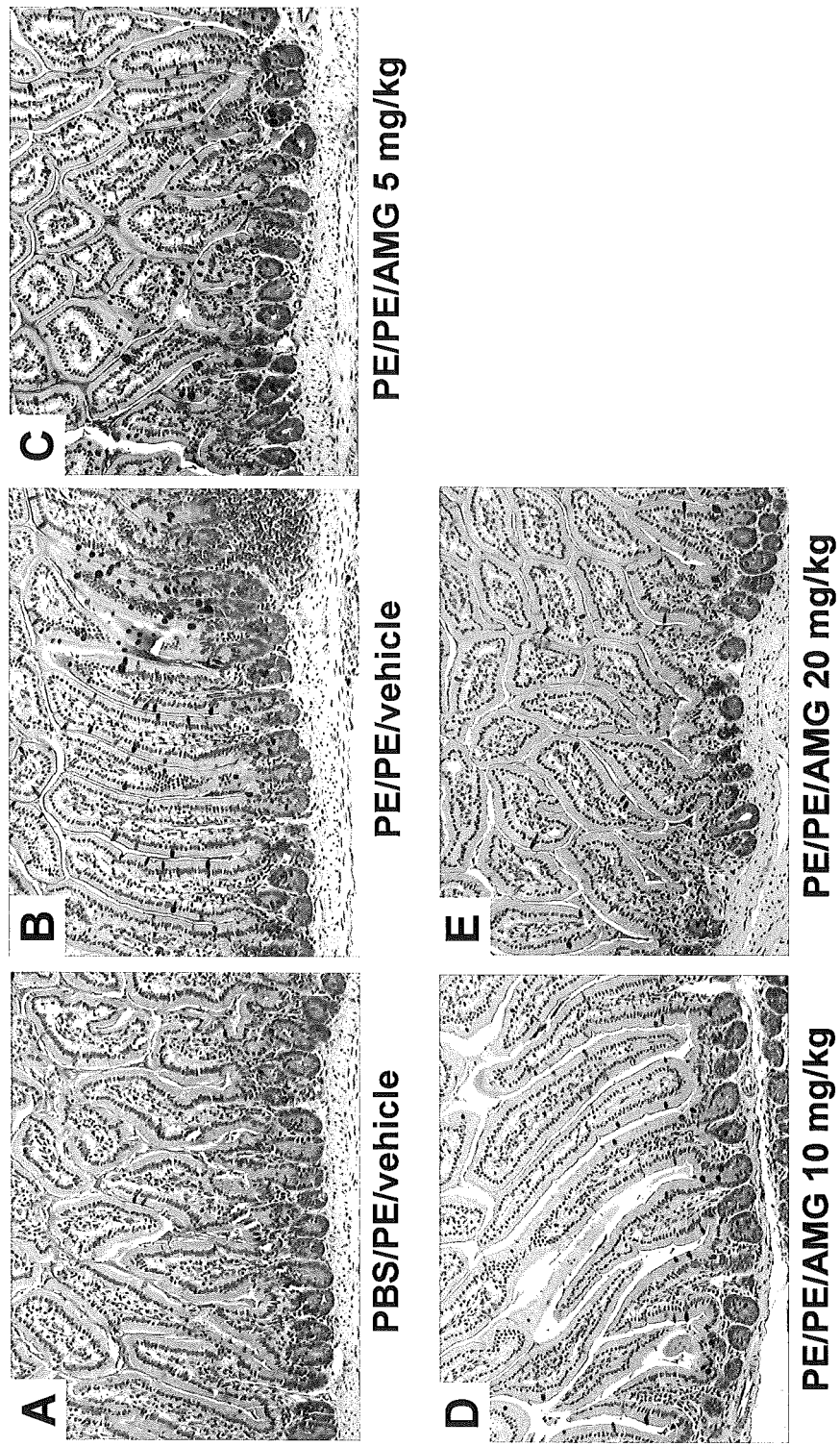
FIG. 13A-E shows the decreased numbers of goblet cells in intestinal epithelium of sensitized and challenged mice treated with AMG. Goblet cells were identified by PAS staining 24 hrs after the last challenge. Representative sections of (A) PBS/PE/vehicle mice, (B) PE/PE/vehicle mice, (C) PE/PE/AMG (5 mg/kg) mice, (D) PE/PE/AMG (10 mg/kg) mice, and (E) PE/PE/AMG (20 mg/kg) mice. Magnification ×200.

To confirm the importance of Cyp11a1 in Th cell differentiation, the inventors used shRNA-mediated silencing of Cyp11a1 in polarized Th2 cells. Polarized Th2 CD4 T cells were transduced with retroviruses co-expressing cyan fluorescent protein (CFP) with control (luciferase) or Cyp11a1 shRNA. Seventy-two hours after transduction, CFP$^+$CD4$^+$ cells were sorted and stimulated with 2 ng/ml anti-CD3/CD28 for 6 and 24 hours. To confirm the effectiveness of Cyp11a1 gene silencing, the inventors demonstrated reduced levels of Cyp11a1 mRNA in Th2 CD4 T cells compared to silencing with the control shRNA (FIG. 11A). As a result, levels of pregnenolone in supernates of cultured Th2 cells transfected with Cyp11a1 shRNA were significantly reduced compared to those transfected with control shRNA (FIG. 11B).

Levels of IL4 and IL13 mRNA were decreased in Th2 CD4 T cells transfected with Cyp11a1 shRNA compared to those transfected with control shRNA, without affecting levels of GATA3 mRNA (FIG. 11C). In parallel, levels of IL-4 and IL-13 were reduced in supernatants of Th2 CD4 T cell cultures transfected with Cyp11a1 shRNA (FIG. 11D). These results demonstrate that silencing of Cyp11a1 in polarized Th2 CD4 T cells resulted in decreased levels of IL4 and IL-13 mRNA and protein without affecting GATA3 transcription. These results indicated that Cyp11a1 upregulation and activation is downstream of GATA3.

All of the documents cited herein are incorporated herein by reference.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following exemplary claims.

REFERENCES

1. Kim, H. Y., et al. The many paths to asthma: phenotype shaped by innate and adaptive immunity. *Nat. Immunol.* 11, 577-584 (2011).
2. Holgate, S. T. Innate and adaptive immune responses in asthma. *Nat. Med.* 18, 673-683 (2012).
3. Gelfand, E. W. and Dakhama, A. CD8$^+$ T lymphocytes and leukotriene B4: Novel interactions in the persistence and progression of asthma. *J. Allergy Clin. Immunol.* 117, 577-582 (2006).
4. Hamelmann, E. et al. Requirement for CD8$^+$ T cells in the development of airway hyperresponsiveness in a murine model of airway sensitization. *J. Exp. Med.* 183, 1719-1729 (1996).
5. Miyahara, N. et al. Contribution of antigen-primed CD8+ T cells to the development of airway hyperresponsiveness and inflammation is associated with IL-13. *J. Immunol.* 172, 2549-2558 (2004).
6. Miyahara, N. et al. Leukotriene B4 (BLT1) is essential for allergen-mediated recruitment of CD8$^+$ T cells and airway hyperresponsiveness. *J. Immunol.* 174, 4979-4984 (2005).
7. Koya, T. et al. CD8$^+$ T cell-mediated airway hyperresponsiveness and inflammation is dependent on CD4$^+$IL-4$^+$ T cells. *J. Immunol.* 179, 2787-2796 (2007).
8. LaVoie, H. A. and King, S. R. Transcriptional regulation of steroidogenic genes: STARD1, CYP11A1 and HSD3B. *Exp. Biol. Med.* 234, 880-907 (2009).
9. Shih, M. C. et al. Mutation of mouse Cyp11a1 promoter caused tissue-specific reduction of gene expression and blunted stress response without affecting reproduction. *Mol. Endocrinol.* 22, 915-923 (2008).
10. National Asthma Education and Prevention Program (National Heart Lung and Blood Institute) Third Expert Panel on the Management of Asthma. National Center for Biotechnology Information (U.S.). Expert panel report 3 guidelines for the diagnosis and management of asthma. Bethesda, Md.: National Institutes of Health National Heart Lung and Blood Institute; 2007. Available from: www.ncbi.nlm.nih.gov/books/bv.fcgi?rid=asthma3.TOC&depth=2.
11. Guidelines for the diagnosis and management of asthma. Bethesda, Md.: National Institutes of Health National Heart Lung and Blood Institute; 2007. Available from: www.ncbi.nlm.nih.gov/books/bv.fcgi?rid=asthma3.TOC&depth=2.
12. Martin, R. J. et al. The predicting response to inhaled corticosteroid efficacy (price) trial. *J. Allergy Clin. Immunol.* 119, 73-80 (2007).
13. Li, L. B. et al. ATF2 impairs glucocorticoid receptor-mediated transactivation in human CD8$^+$ T cells. *Blood* 110, 1570-1577 (2007).
14. Payne, A. H. Hormonal regulation of cytochrome P450 enzymes, cholesterol side-chain cleavage and 17 alpha-hydroxylase/C17-20 lyase in Leydig cells. *Biol. Reprod.* 42, 399-404 (1990).
15. van Rensen, E. L. et al. Bronchial CD8 cell infiltrate and lung function decline in asthma. *Am. J. Respir. Crit. Care Med.* 172, 837-841 (2005).
16. Mosmann, T. R., and Coffman, R. L. TH1 and TH2 cells: different patterns of lymphokine secretion lead to different functional properties. *Annu. Rev. Immunol.* 7, 145-173 (1989).
17. Seder, R. A. et al. D8$^+$ T cells can be primed in vitro to produce IL-4. *J. Immunol.* 148, 1652-1656 (1992).
18. Croft, M. et al. Generation of polarized antigen-specific CD8 effector populations: reciprocal action of interleukin (IL)-4 and IL-12 in promoting type 2 versus type 1 cytokine profiles. *J. Exp. Med.* 180, 1715-1728 (1994).
19. Pestell, R. G. et al. Stimulation of the P-450 side chain cleavage enzyme (CYP11A1) promoter through ras- and Ets-2-signaling pathways. *Mol. Endocrinol.* 10, 1084-1094 (1996).
20. Al Kandari, H. et al. Homozygous mutation of P450 side-chain cleavage enzyme gene (CYP11A1) in 46, XY patient with adrenal insufficiency, complete sex reversal, and agenesis of corpus callosum. *J. Clin. Endocr. Metab.* 91, 2821-2826 (2006).
21. Kim, C. J. et al. Severe combined adrenal and gonadal deficiency caused by novel mutations in the cholesterol side-chain cleavage enzyme, P450scc. *J. Clin. Endocrinol. Metab.* 93, 696-702 (2008).
22. Robel, P. et al. Biosynthesis and assay of neurosteroids in rats and mice. *J. Steroid Biochem. Molec. Biol.* 53, 355-360 (1995).
23. Slominski, A. et al. An alternative pathway of vitamin D metabolism. Cytochrome P450scc (CYP11A1)-mediated conversion to 20-hydroxyvitamin D2 and 17, 20-dihydroxyvitamin D2. *FEBS J.* 273, 2891-2901 (2006).

24. Oka, H. et al. Breakdown of Th cell immune responses and steroidogenic CYP11A1 expression in CD4+ T cells in a murine model implanted with B16 melanoma. *Cell. Immunol.* 206, 7-15 (2000).
25. Sundrud, M. S, and Nolan, M. A. Synergistic and combinatorial control of T cell activation and differentiation by transcription factors. *Curr. Opin. Immunol.* 22, 286-292 (2010).
26. Amsen, D. et al. How are T(H)1 and T(H)2 effector cells made? *Curr. Opin. Immunol.* 21, 153-160 (2009).
27. Miyahara, N. et al. Effector memory CD8+ T cells mediate airway hyperresponsiveness, inflammation and remodeling. *Nature Med.* 10, 865-869 (2004).
28. Ohnishi, H. et al. Corticosteroids enhance CD8+ T cell-mediated airway hyperresponsiveness and allergic inflammation by upregulating leukotriene B4 receptor 1. *J. Allergy Clin. Immunol.* 121, 864-871 (2008).
29. Samy, T. S. et al. Divergent immune responses in male and female mice after trauma-hemorrhage: Dimorphic alterations in T lymphocyte steroidogenic enzyme activities. *Endocrinology* 142, 3519-3529 (2001).
30. Pottratz, S. T. et al. 17-Estradiol inhibits expression of human interleukin-6 promoter-receptor constructs by a receptor-dependent mechanism. *J. Clin. Invest.* 93, 944-950 (1994).
31. De Bosscher, K., Vanden Berghe, W., & Haegeman, G. The interplay between the glucocorticoid receptor and nuclear factor-kappaB or activator protein-1: molecular mechanisms for gene repression. *Endocr. Rev.* 24, 488-522 (2003).
32. De Bosscher, K, & Haegeman, G. Minireview: latest perspectives on antiinflammatory actions of glucocorticoids. *Mol. Endocrinol.* 23, 281-291 (2009).
33. Chrousos, G. P. The hypothalamic-pituitary-adrenal axis and immune-mediated inflammation. *N. Engl. J. Med.* 332, 1351-1362 (1995).
34. Barnes, P J. Glucocorticosteroids: current and future directions. *Br. J. Pharmacol.* 163:29-43 (2011).
35. Faubion, W. A. Jr., Loftus, E. V. Jr., Harmsen, W. S., Zinsmeister, A. R., & Sandborn, W. J. The natural history of corticosteroid therapy for inflammatory bowel disease: a population-based study. *Gastroenterology* 121, 255-260 (2001).
36. Cima, I., et al. Intestinal epithelial cells synthesize glucocorticoids and regulate T cell activation. *J. Exp. Med.* 200, 1635-1646 (2004).
37. Ohnishi, H., et al. Corticosteroids enhance CD8+ T cell-mediated airway hyperresponsiveness and allergic inflammation by upregulating leukotriene B4 receptor 1. *J. Allergy Clin. Immunol.* 121, 864-871 (2008).
38. Payne, A. H. Hormonal regulation of cytochrome P450 enzymes, cholesterol side-chain cleavage and 17 alpha-hydroxylase/C17-20 lyase in Leydig cells. *Biol. Reprod.* 42, 399-404 (1990).
39. Pazirandeh, A., et al. Paracrine glucocorticoid activity produced by mouse thymic epithelial cells. *FASEB J.* 13, 893-901 (1999).
40. Shih, M. C., Chiu, Y. N., Hu, M. C., Guo, I. C., & Chung, B. C. Regulation of steroid production: analysis of Cyp11a1 promoter. *Mol. Cell. Endocrinol.* 336, 80-84 (2011).
41. Pang, S., et al. Inherited congenital adrenal hyperplasia in the rabbit: absent cholesterol side-chain cleavage cytochrome P450 gene expression. *Endocrinology* 131, 181-186 (1992).
42. Yang, X., et al. Inherited congenital adrenal hyperplasia in the rabbit is caused by a deletion in the gene encoding cytochrome P450 cholesterol side-chain cleavage enzyme. *Endocrinology* 132, 1977-1982 (1993).
43. Kim, C. J., et al. Severe combined adrenal and gonadal deficiency caused by novel mutations in the cholesterol side chain cleavage enzyme, P450scc. *J. Clin. Endocrinol. Metab.* 93, 696-702 (2008).
44. Al Kandari, H., Katsumata, N., Alexander, S., & Rasoul, M. A. Homozygous mutation of P450 side-chain cleavage enzyme gene (CYP11A1) in 46, XY patient with adrenal insufficiency, complete sex reversal, and agenesis of corpus callosum. *J. Clin. Endocrinol. Metab.* 91, 2821-2826 (2006).
45. Tajima, T., Fujieda, K., Kouda, N., Nakae, J., & Miller, W. L. Heterozygous mutation in the cholesterol side chain cleavage enzyme (p450scc) gene in a patient with 46, XY sex reversal and adrenal insufficiency. *J. Clin. Endocrinol. Metab.* 86, 3820-3825 (2001).
46. Parajes, S., et al. A novel entity of clinically isolated adrenal insufficiency caused by a partially inactivating mutation of the gene encoding for P450 side chain cleavage enzyme (CYP11A1). *J. Clin. Endocrinol. Metab.* 96, E1798-E1806 (2011).
47. Dexter, R. N., Fishman, L. M., Ney, R. L., & Liddle, G. W. Inhibition of adrenal corticosteroid synthesis by aminoglutethimide: studies of the mechanism of action. *J. Clin. Endocrinol. Metab.* 27, 473-480 (1967).
48. Wang, M., et al. Peanut-induced intestinal allergy is mediated through a mast cell-IgE-FcepsilonRI-IL-13 pathway. *J. Allergy Clin. Immunol.* 126, 306-316 (2010).
49. Brandt, E. B., et al. Mast cells are required for experimental oral allergen-induced diarrhea. *J. Clin. Invest.* 112, 1666-1677 (2003).
50. Wang, M., et al Inhibition of Pim1 kinase prevents peanut allergy by enhancing Runx3 expression and suppressing T(H)2 and T(H)17 T-cell differentiation. *J. Allergy Clin. Immunol.* 130, 932-944 (2012).
51. Wills-Karp, M., et al. Interleukin-13: central mediator of allergic asthma. *Science* 282, 2258-2261 (1998).
52. Corren, J., et al. Lebrikizumab treatment in adults with asthma. *N. Engl. J. Med.* 365, 1088-1098 (2011).
53. Kolls, J. K., & Linden, A. Interleukin-17 family members and inflammation. *Immunity* 21, 467-476 (2004).
54. Lajoie, S., et al. Complement-mediated regulation of the IL-17A axis is a central genetic determinant of the severity of experimental allergic asthma. *Nature Immunol.* 11, 928-935 (2010).
55. Zhu, J., Yamane, H., & Paul, W. E. Differentiation of effector CD4 T cell populations. *Annu. Rev. Immunol.* 28, 445-489 (2010).
56. Islam, S. A., & Luster, A. D. T cell homing to epithelial barriers in allergic disease. *Nature Med.* 18, 705-715 (2012).
57. Knight, A. K., et al. CD4 T cells activated in the mesenteric lymph node mediate gastrointestinal food allergy in mice. *Am. J. Physiol. Gastrointest. Liver Physiol.* 293, G1234-G1243 (2007).
58. Prussin, C., Lee, J., & Foster, B. Eosinophilic gastrointestinal disease and peanut allergy are alternatively associated with IL-5+ and IL-5− TH2 responses. *J. Allergy Clin. Immunol.* 124, 1326-1332 (2009).
59. DeLong, J. H., et al. Ara h 1-reactive T cells in individuals with peanut allergy. *J. Allergy Clin. Immunol.* 127, 1211-1218 (2011).
60. Beyer, K., et al. Human milk-specific mucosal lymphocytes of the gastrointestinal tract display a TH2 cytokine profile. *J. Allergy Clin. Immunol.* 109, 707-713 (2002).

61. Rhen, T., & Cidlowski, J. A. Antiinflammatory action of glucocorticoids-new mechanisms for old drugs. *N. Engl. J. Med.* 353, 1711-1723 (2005).
62. Mueller, M., et al. The nuclear receptor LRH-1 critically regulates extra-adrenal glucocorticoid synthesis in the intestine. *J. Exp. Med.* 203, 2057-2062 (2006).
63. Cima, I., Fuhrer, A., & Brunner, T. Antagonistic and synergistic effects of glucocorticoids and IL-7 on CD4+ T cell activation. *Immunol. Lett.* 106, 99-102 (2006).
64. LaVoie, H. A., & King, S. R. Transcriptional regulation of steroidogenic genes: STARD1, CYP11A1 and HSD3B. *Exp. Biol. Med.* 234, 880-907 (2009).
65. Wei, G, et al. Genome-wide analyses of transcription factor GATA3-mediated gene regulation in distinct T cell types. *Immunity* 35, 299-311 (2011).
66. Sher, N., Yivgi-Ohana, N., & Orly, J. Transcriptional regulation of the cholesterol side chain cleavage cytochrome P450 gene (CYP11A1) revisited: binding of GATA, cyclic adenosine 3',5'-monophosphate response element-binding protein and activating protein (AP)-1 proteins to a distal novel cluster of cis-regulatory elements potentiates AP-2 and steroidogenic factor-1-dependent gene expression in the rodent placenta and ovary. *Mol. Endocrinol.* 21, 948-962 (2007).
67. Oka, H., Emori, Y, Hayashi, Y., & Nomoto, K. Breakdown of Th cell immune responses and steroidogenic CYP11A1 expression in CD4+ T cells in a murine model implanted with B16 melanoma. *Cell. Immunol.* 206, 7-15 (2000).
68. Li, X. M., et al. A murine model of peanut anaphylaxis: T- and B-cell responses to a major peanut allergen mimic human responses. *J. Allergy Clin. Immunol.* 106, 150-158 (2000).
69. Tomkinson, A., et al. Temporal association between airway hyperresponsiveness and airway eosinophilia in ovalbumin-sensitized mice. *Am. J. Respir. Crit. Care Med.* 163, 721-730 (2001).
70. Komine, O., et al. The Runx1 transcription factor inhibits the differentiation of naive CD4+ T cells into the Th2 lineage by repressing GATA3 expression. *J. Exp. Med.* 198, 51-61 (2003).
71. Ashino, S., et al. A T(h)17-polarized cell population that has infiltrated the lung requires cells that convert to IFN-{gamma} production in order to induce airway hyperresponsiveness. *Intl. Immunol.* 22, 503-513 (2010).
72. Musselman, C. A., et al. Bivalent recognition of nucleosomes by the tandem PHD fingers of the CHD4 ATPase is required for CHD4-mediated repression. *Proc. Natl. Acad. Sci. USA* 109, 787-792 (2012).
73. Maier, H., et al. Requirements for selective recruitment of Ets proteins and activation of mb-1/Ig-alpha gene transcription by Pax-5 (BSAP). *Nucleic Acids Res.* 31, 5483-5489 (2003).
74. Pham, D., Vincentz, J. W., Firulli, A. B., & Kaplan, M. H. Twist1 regulates IFN expression in Th1 cells by interfering with Runx3 function. *J. Immunol.* 189, 832-840 (2012).
75. Wang, M., et al. Peanut-induced intestinal allergy is mediated through a mast cell-IgE-FcepsilonRI-IL-13 pathway. *J. Allergy Clin. Immunol.* 126:306-316 (2010).
76. Li, X. M., et al. A murine model of peanut anaphylaxis: T- and B-cell responses to a major peanut allergen mimic human responses. *J. Allergy Clin. Immunol.* 106:150-158 (2000).
77. Ashino, S., et al. A T(h)17-polarized cell population that has infiltrated the lung requires cells that convert to IFN-{gamma} production in order to induce airway hyperresponsiveness. *Intl. Immunol.* 22:503-513 (2010).
78. Ohnishi, H., et al. Corticosteroids enhance CD8+ T cell-mediated airway hyperresponsiveness and allergic inflammation by upregulating leukotriene B4 receptor 1. *J. Allergy Clin. Immunol.* 121:864-871 (2008).

What is claimed is:

1. A method of treating an allergic disease selected from the group consisting of an allergic lung disease, allergen-induced airway hyperresponsiveness, allergen-induced inflammation, asthma, and food allergy, in a subject who has, or is at risk of developing an allergic disease, comprising administering to the subject a therapeutically effective amount of a steroidogenic pathway inhibitor, wherein the steroidogenic pathway inhibitor inhibits cytochrome P450 family 11 subfamily A polypeptide 1 (Cyp11A1) enzyme activity, and wherein the steroidogenic pathway inhibitor is aminoglutethimide.

2. The method of claim 1, wherein the allergic disease is caused by one or more proteinaceous allergens.

3. The method of claim 1, wherein the subject has been sensitized to an allergen or is at risk of becoming exposed to an allergen.

4. The method of claim 1, wherein the food allergy is peanut allergy.

5. The method of claim 1, wherein the allergic disease is an allergic lung disease.

6. A method of inhibiting T-cell pro-allergic differentiation in a subject having an allergic disease comprising administering to the subject a therapeutically effective amount of a steroidogenic pathway inhibitor, wherein the steroidogenic pathway inhibitor inhibits cytochrome P450 family 11 subfamily A polypeptide 1 (Cyp11A1) enzyme activity, and wherein the steroidogenic pathway inhibitor is aminoglutethimide.

7. The method of claim 6, wherein the T-cell pro-allergic differentiation is CD4+ T-cells to Th2 and Th17 cell differentiation.

8. The method of claim 6, wherein the T-cell pro-allergic differentiation is CD8+ T-cells to Tc2 cell differentiation.

9. The method of claim 6, wherein the T-cell pro-allergic differentiation is IL4-induced conversion of CD8+ T-cells into IL-13 secreting cells.

10. The method of claim 6, wherein the T-cell pro-allergic differentiation is IL-4 induced conversion of CD4+ T-cells into IL-13 secreting cells.

11. The method of claim 6, wherein the allergic disease selected from the group consisting of a allergic lung disease, allergen-induced airway hyperresponsiveness, allergen-induced inflammation, rhinitis, asthma, allergic rhinitis, food allergy, eosinophilic esophagitis, chronic urticaria, atopic dermatitis, occupational allergy, allergic conjunctivitis, hay fever, airborne allergic sensitivities, stinging insect allergy, hypersensitivity pneumonitis, eosinophilic lung diseases, inflammatory bowel disease, ulcerative colitis, and Crohn's disease.

12. The method of claim 11, wherein the allergic disease is caused by one or more proteinaceous allergens.

13. The method of claim 11, wherein the food allergy is peanut allergy.

14. The method of claim 11, wherein the allergic disease is allergic lung disease.

* * * * *

```
                          SEQUENCE LISTING

<160> NUMBER OF SEQ ID NOS: 3

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Ser Ile Ile Asn Phe Glu Lys Leu
1               5

<210> SEQ ID NO 2
<211> LENGTH: 55
<212> TYPE: DNA
<213> ORGANISM: Artificial Sequence
<220> FEATURE:
<223> OTHER INFORMATION: Synthetic primer

<400> SEQUENCE: 2
ttcaataaag ctgatgagta ttcaagagat actcatcagc tttattgatt ttttc          55

<210> SEQ ID NO 3
<211> LENGTH: 59
<212> TYPE: DNA
<213> ORGANISM: Artificial Sequence
<220> FEATURE:
```

-continued

```
<223> OTHER INFORMATION: Synthetic primer

<400> SEQUENCE: 3
tcgagaaaaa atcaataaag ctgatgagta tctcttgaat actcatcagc tttattgaa      59
```